(12) United States Patent
Anderson et al.

(10) Patent No.: US 12,582,364 B2
(45) Date of Patent: Mar. 24, 2026

(54) SYSTEMS AND METHODS FOR PASSIVE COLLISION CONTROL DURING MEDICAL IMAGING OR THERAPEUTIC PROCEDURES

(71) Applicant: INNOVERE MEDICAL INC., Markham (CA)

(72) Inventors: Kevan James Thompson Anderson, Cobourg (CA); Lisa Margaret Cooper, North York (CA); David Robert Green, Toronto (CA); Gareth Alan Kenworthy, Stouffville (CA); Garry Ka Chun Liu, Toronto (CA); Donald Bruce Plewes, Toronto (CA)

(73) Assignee: INNOVERE MEDICAL INC., Markham (CA)

( * ) Notice: Subject to any disclaimer, the term of this patent is extended or adjusted under 35 U.S.C. 154(b) by 356 days.

(21) Appl. No.: 17/781,107

(22) PCT Filed: Nov. 27, 2020

(86) PCT No.: PCT/CA2020/051636
§ 371 (c)(1),
(2) Date: May 31, 2022

(87) PCT Pub. No.: WO2021/102587
PCT Pub. Date: Jun. 3, 2021

(65) Prior Publication Data
US 2022/0409149 A1 Dec. 29, 2022

Related U.S. Application Data

(60) Provisional application No. 62/942,048, filed on Nov. 29, 2019.

(51) Int. Cl.
| A61B 6/04 | (2006.01) |
| G01R 33/20 | (2006.01) |
| G01R 33/28 | (2006.01) |

(52) U.S. Cl.
CPC ............... *A61B 6/04* (2013.01); *G01R 33/20* (2013.01); *G01R 33/283* (2013.01)

(58) Field of Classification Search
CPC .......... A61B 6/04; A61B 6/102; G01R 33/20; G01R 33/283; G01R 33/28
See application file for complete search history.

(56) References Cited

U.S. PATENT DOCUMENTS

| 6,651,279 | B1 | 11/2003 | Muthuvelan |
| 8,363,861 | B2 | 1/2013 | Hughes et al. |

(Continued)

FOREIGN PATENT DOCUMENTS

WO 2019068185 A1 4/2019

OTHER PUBLICATIONS

International Search Report dated Apr. 8, 2021, for PCT/CA2020/051636 filed Nov. 27, 2020.

*Primary Examiner* — David J Makiya
*Assistant Examiner* — Mamadou Faye
(74) *Attorney, Agent, or Firm* — Stephen Leonard; Aird & McBurney LP

(57) ABSTRACT

Systems and methods are provided for managing and reducing the severity or impact of a collision involving an apparatus secured to a table associated with a medical imaging and/or therapeutic gantry. Example systems are provided in which an apparatus is secured to the table such that a distal region of the apparatus extends beyond a longitudinal end of the table. A pivot joint associated with the apparatus is provided such that when a collision between the distal region of the apparatus and an object occurs due (Continued)

to motion of the table, the resulting force causes the apparatus to rotate relative to the pivot joint, thus passively accommodating the applied force and preventing, or reducing the likelihood of, mechanical buckling of the apparatus in the presence of the force. In some example embodiments, the apparatus is configured to rotate and/or translate as a result of the force applied during the collision.

27 Claims, 20 Drawing Sheets

(56)                    References Cited

U.S. PATENT DOCUMENTS

| | | | |
|---|---|---|---|
| 8,975,894 B2 | 3/2015 | Lee | |
| 2006/0133573 A1 | 6/2006 | Wong et al. | |
| 2014/0039351 A1* | 2/2014 | Mix | G16H 40/20 |
| | | | 600/587 |
| 2014/0163736 A1 | 6/2014 | Azizian et al. | |
| 2014/0340828 A1* | 11/2014 | Truong | G06F 1/1601 |
| | | | 248/122.1 |
| 2015/0131775 A1* | 5/2015 | Yorkston | A61B 6/4405 |
| | | | 378/17 |
| 2015/0157080 A1* | 6/2015 | Camarillo | A42B 3/122 |
| | | | 2/459 |
| 2016/0296185 A1* | 10/2016 | Gemmel | A61B 6/547 |
| 2017/0086309 A1* | 3/2017 | Brandes | F16M 11/00 |
| 2019/0307423 A1* | 10/2019 | Han | F16M 13/022 |
| 2019/0343469 A1* | 11/2019 | Inoue | A61B 90/39 |

* cited by examiner

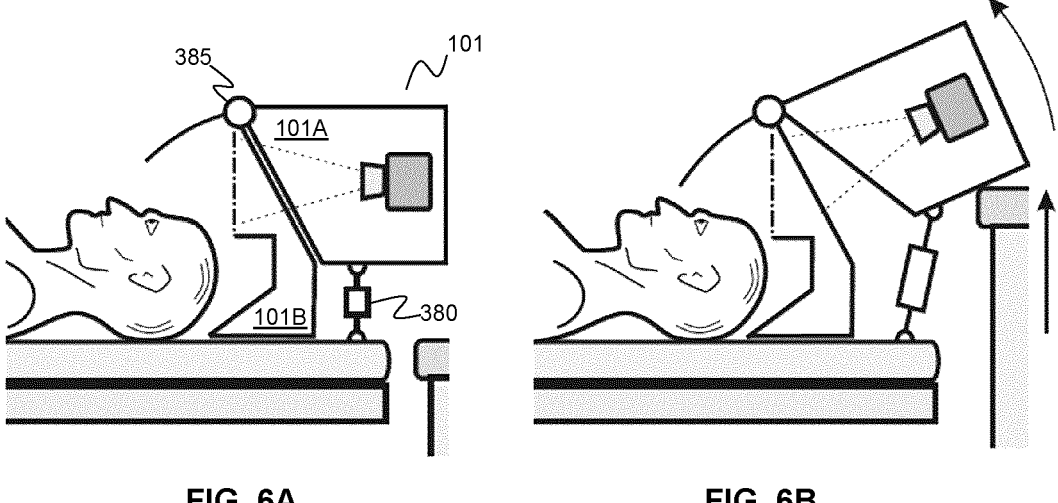
FIG. 6A                    FIG. 6B
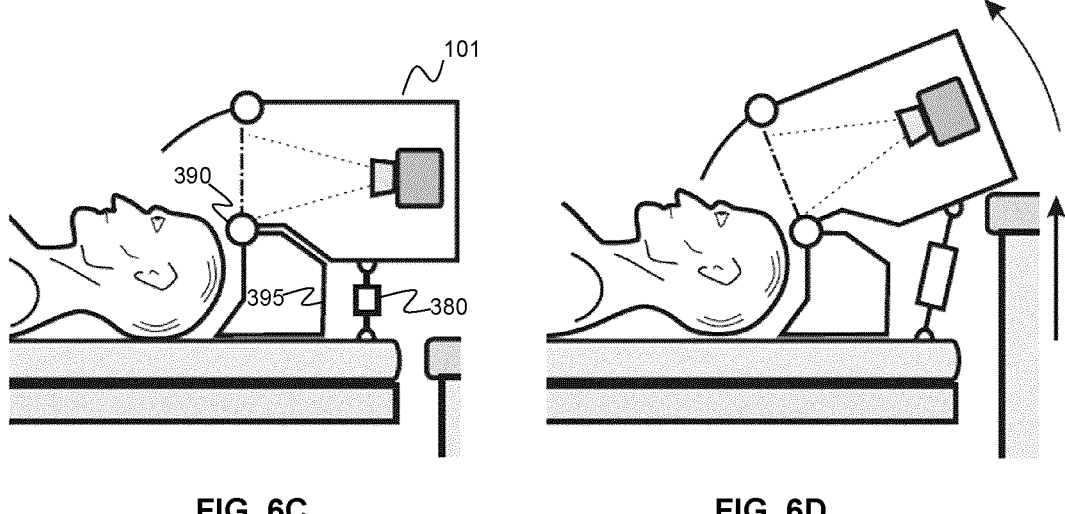
FIG. 6C                    FIG. 6D

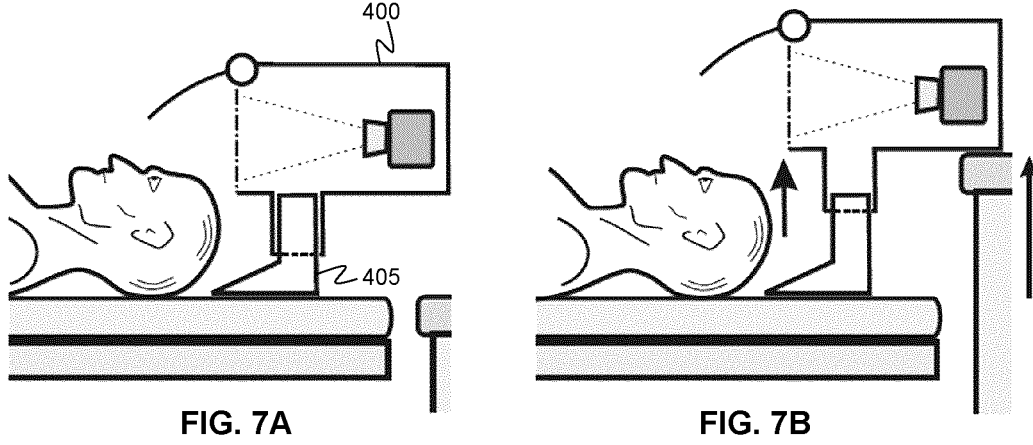
FIG. 7A                              FIG. 7B
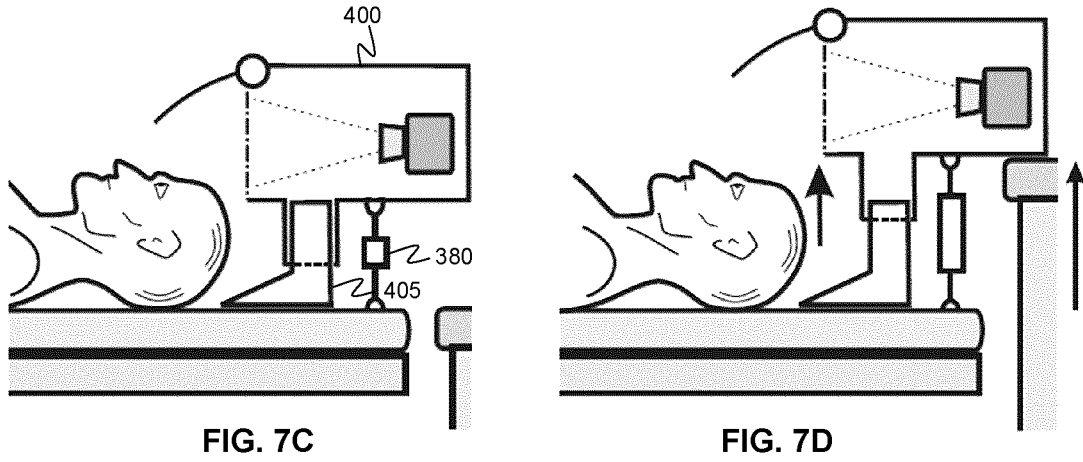
FIG. 7C                              FIG. 7D

101

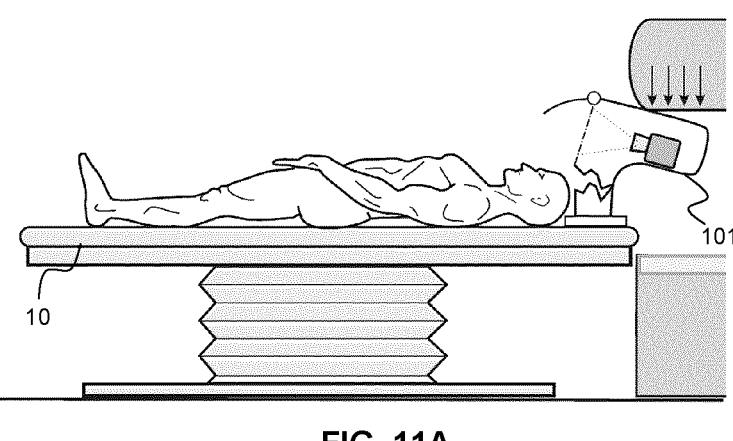
FIG. 11A
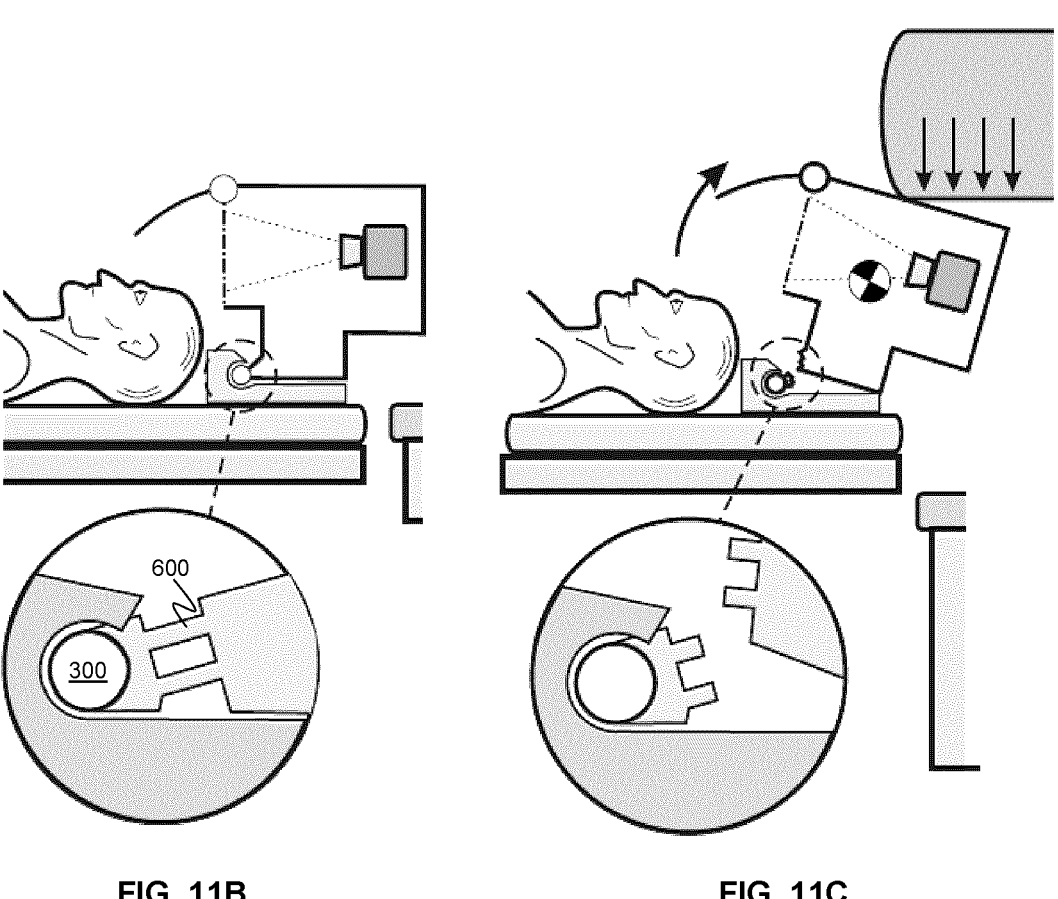
FIG. 11B                    FIG. 11C

SYSTEMS AND METHODS FOR PASSIVE COLLISION CONTROL DURING MEDICAL IMAGING OR THERAPEUTIC PROCEDURES

CROSS-REFERENCE TO RELATED APPLICATION

This application is a National Phase application claiming the benefit of the international PCT Patent Application No. PCT/CA2020/051636, filed on Nov. 27, 2020, in English, which claims priority to U.S. Provisional Application No. 62/942,048, titled "SYSTEMS AND METHODS FOR PASSIVE COLLISION CONTROL DURING MEDICAL IMAGING OR THERAPEUTIC PROCEDURES" and filed on Nov. 29, 2019, the entire contents of which are incorporated herein by reference.

BACKGROUND

The present disclosure relates to gantry-based medical imaging systems and medical therapeutic systems. More particularly, the present disclosure relates to managing collisions involving gantry-based medical imaging systems and medical therapeutic systems.

Many medical imaging and therapeutic systems, such as magnetic resonance imaging systems and radiation treatment systems, employ a configuration in which a medical imaging or therapeutic device includes a gantry. Such systems typically employ a positionable table (also commonly referred to as a couch) to facilitate the positioning of the patient relative to the gantry and can be prone to collisions involving the table.

SUMMARY

Systems and methods are provided for managing and reducing the severity or impact of a collision involving an apparatus secured to a table associated with a medical imaging and/or therapeutic gantry. Example systems are provided in which an apparatus is secured to the table such that a distal region of the apparatus extends beyond a longitudinal end of the table. A pivot joint associated with the apparatus is provided such that when a collision between the distal region of the apparatus and an object occurs due to motion of the table, the resulting force causes the apparatus to rotate relative to the pivot joint, thus passively accommodating the applied force and preventing, or reducing the likelihood of, mechanical buckling of the apparatus in the presence of the force. In some example embodiments, the apparatus is configured to rotate and/or translate as a result of the force applied during the collision.

According, in a first aspect, there is provided medical imaging and/or therapeutic system comprising:

a gantry supporting a medical imaging device or a medical therapeutic device;

a table translatable relative to the gantry; and an apparatus secured to the table such that a distal portion of the apparatus extends beyond a longitudinal end of the table;

the system comprising a pivot joint, the pivot joint being located such that when a force is applied to the distal portion during a collision involving contact of the distal portion with an object during motion of the table, the force results in rotation of a rotatable portion of the apparatus about the pivot joint, the rotatable portion comprising at least the distal portion of the apparatus.

In some example implementations of the system, the apparatus is configured such that when the collision is a vertical collision resulting from downward motion of the table and the force comprises an upwardly-directed force, the rotatable portion rotates about the pivot joint in response to application of the upwardly-directed force. The apparatus may be configured such that when the table is retracted from the gantry with the distal portion residing above an edge of the gantry, and wherein the upwardly-directed force results from contact of the distal portion with the edge of the gantry during the downward motion of the table, the rotatable portion rotates about the pivot joint in response to application of the upwardly-directed force.

In some example implementations of the system, the apparatus is configured such that when the collision is a horizontal collision resulting from horizontal motion of the table and the force is a horizontally-directed force, the rotatable portion rotates about the pivot joint in response to application of the horizontally-directed force. A center of gravity of the rotatable portion of the apparatus may be located such that when the object is a wall and the longitudinal end of the table contacts the wall during the horizontal collision, thereby preventing further horizontal translation of the apparatus, a gravitational torque applied to the rotatable portion opposes further rotation of the rotatable portion.

In some example implementations of the system, the apparatus is secured to the table through a connection member, and wherein the apparatus is pivotally coupled to the connection member through the pivot joint.

In some example implementations of the system, the apparatus is secured to the table through a pair of connection members that are respectively received within a first channel of the table and a second channel of the table, and wherein the apparatus is pivotally coupled to each connection member through a respective pivot joint.

In some example implementations of the system, the pivot joint is located at an intermediate location within the apparatus. The intermediate location may reside along an upper surface of the apparatus. The pivot joint may be located such that the rotatable portion comprises one or more electrical components and wherein a remaining non-rotatable portion of the apparatus is absent of active electrical components. The rotatable portion may be a first rotatable portion and the pivot joint is a first pivot joint, the system further comprising a second rotatable portion that is pivotally connected to the first rotatable portion through the first pivot joint, and wherein the second rotatable portion is pivotally connected to the table through a second pivot joint, such that both the first rotatable portion and the second rotatable portion are rotatable in response to application of the force.

In some example implementations of the system, the system further comprises a restoring means for applying a restoring torque to the rotatable portion of the apparatus. The restoring means may include an elastic member connecting the rotatable portion to a non-rotatable portion of the system. The restoring means may include a damping member connecting the rotatable portion to a non-rotatable portion of the system. The restoring means may include a torsion spring.

In some example implementations of the system, the apparatus is pivotally coupled to the table by at least two adjacent pivot bars, each pivot bar being pivotally coupled to the apparatus and pivotally coupled to the table, such that under application of the force, the at least two adjacent pivot bars rotate in parallel and the rotatable portion of the apparatus is rotated and translated.

In some example implementations of the system, the system further comprises a stop means for arresting rotation of the rotatable portion beyond a pre-selected rotation angle.

The stop means may include a structural member configured to arrest rotation of the rotatable portion beyond the pre-selected rotation angle. The structural member may be attached to the rotatable portion of the apparatus such that rotation of the rotatable portion is arrested upon contact of the structural member with the table. The structural member may be attached to table such that rotation of the rotatable portion is arrested upon contact of the structural member with the rotatable portion of the apparatus.

The stop means may include a cable connecting the rotatable portion to a non-rotatable portion of the system such that the cable becomes taught when the rotatable portion is rotated to the pre-selected rotation angle.

The pre-selected rotation angle may be selected to avoid contact of the apparatus with a subject when the subject is positioned on the table such that a distal portion of the subject resides adjacent to the apparatus.

In some example implementations of the system, the system includes a resistance means for resisting rotation of the rotatable portion beyond a pre-selected rotation angle. The resistance means may include a compressible stop. The resistance means may include an elastic cable connecting the rotatable portion to a non-rotatable portion of the system such that the elastic cable becomes taught when the rotatable portion is rotated to the pre-selected rotation angle.

In some example implementations of the system, the apparatus is configured such when the force is applied to the distal portion during the collision involving contact of the distal portion with the object during motion of the table, the force results in translation of at least the rotatable portion in addition to rotation of the rotatable portion of the apparatus about the pivot joint. The apparatus may include a first portion that is secured to the table and a second portion that is telescopically extendable from the first portion when the force is applied to the distal portion.

In some example implementations of the system, the apparatus is configured such that when the collision is a vertical collision resulting from upward motion of the table and the force is a downwardly-directed force, the apparatus is configured to detach from the pivot joint when the downwardly-directed force exceeds a threshold force.

In some example implementations of the system, the apparatus is a display apparatus for displaying images during a medical imaging or therapeutic procedure.

In another aspect, there is provided a medical imaging and/or therapeutic system comprising:

a gantry supporting a medical imaging device or a medical therapeutic device;

a table translatable relative to the gantry; and an apparatus comprising:

a first portion secured to the table; and a second portion that is translatable, in a vertical direction, relative to the first portion, the second portion comprising a distal region that extends beyond a longitudinal end of the table, such that when a force is applied to the distal region of the second portion during a collision involving contact of the distal region with an object during motion of the table, the force results in translation of the second portion relative to the first portion.

In another aspect, there is provided a display system comprising:

a support frame;

an attachment mechanism comprising a pivot joint for pivotally securing the support frame to a table;

a display subsystem supported by the support frame, wherein the display system is configured such that when the support frame is attached to a table and a subject resides on the table, images displayed by the display subsystem are viewable by the subject;

the attachment mechanism being configured such that when the support frame is attached to the table with a distal portion of display system extending beyond a longitudinal end of the table, a force applied during a collision involving contact of the distal portion with an object during motion of the table results in rotation of a rotatable portion of the display system about the pivot joint.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 6A-6D illustrate several additional example embodiments in which at least a portion of the apparatus is capable of rotating under application of an external force during a collision, where the pivot joint is provided at an intermediate location of the apparatus.

FIGS. 7A-7D illustrate several example embodiments in which at least a portion of the apparatus is capable of translating under application of an external force during a collision.

FIG. 11A illustrates a vertical collision that occurs due to upward motion of the table, such that a distal portion of the apparatus that extends beyond the longitudinal end of the table contacts an upper inner surface of the gantry.

FIGS. 11B and 11C show an example embodiment in which the apparatus is configured to detach from the pivot joint when a downwardly-directed force exceeds a threshold force.

DETAILED DESCRIPTION

Figure 1:
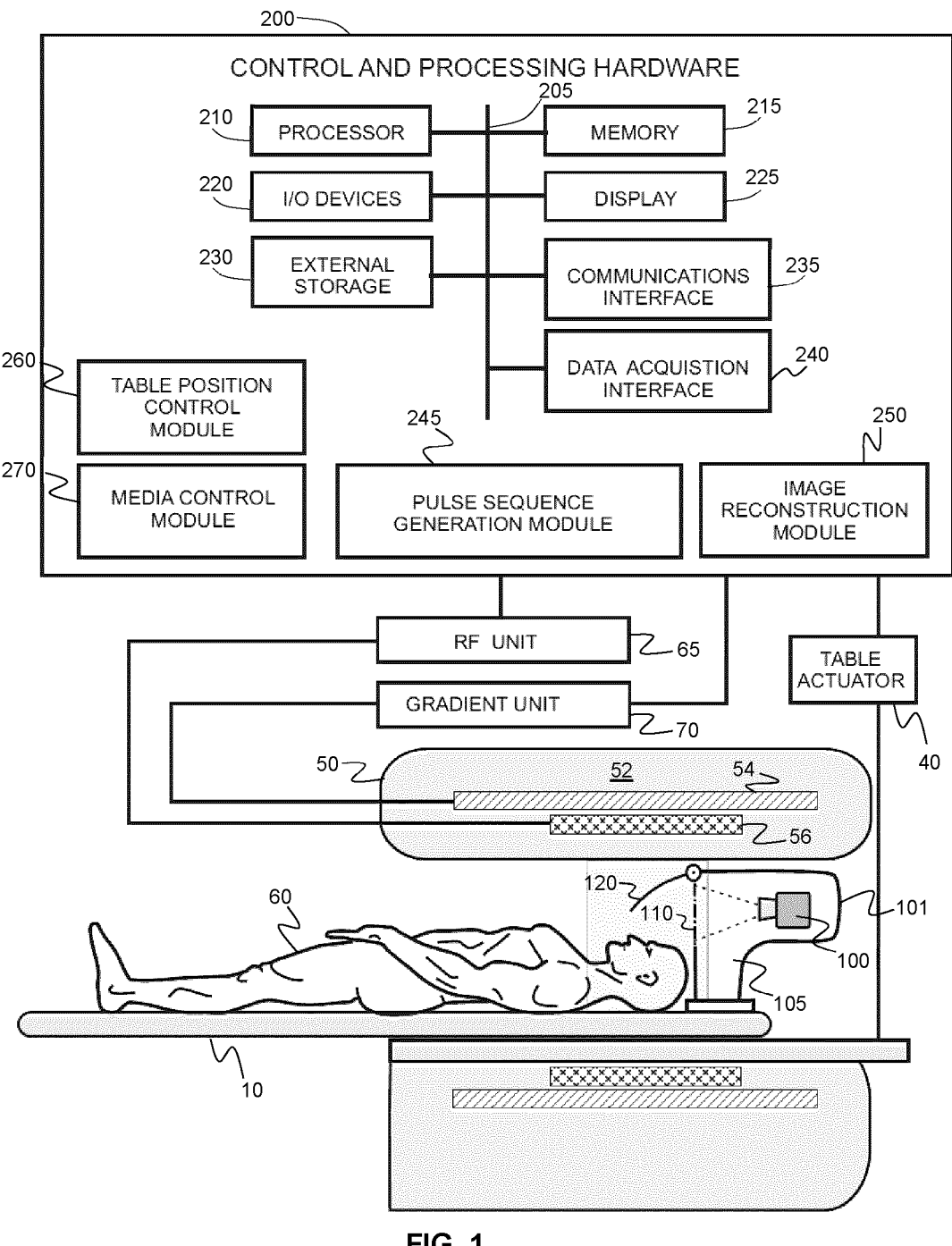
FIGS. 1 and 2 shows examples of a magnetic resonance imaging system that is adapted to display images to a patient within the scanner bore.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

The phrase "gantry", as used herein, is intended to refer to any mechanical support system that is employed to support a medical imaging and/or medical therapeutic device relative to a movable table. Although the preceding example illustrate a closed gantry in the form of a magnetic resonance imaging gantry having a central bore in which a patient can be translated on a table such that the patient is azimuthally surrounded by the gantry, it will be understood that the gantry need not completely surround the patient. For example, a magnetic resonance imaging gantry may be a so-called "open bore" gantry that does not completely surround the patient. In the example embodiments listed above that do not involve magnetic resonance imaging, the gantry may be, for example, a C-arm or an O-arm. In other example embodiments, such as examples involving robotic surgical procedures, the gantry may be mechanical linkage that is controllable to position a medical device or instrument relative to a patient that is positionable on a table.

In the context of magnetic resonance imaging (MRI), devices and accessories for MRI systems have traditionally been placed outside of the MRI bore. Examples of such devices include screens for displaying images and videos to patient for FMRI and entertainment. Devices and accessories can also be mounted on the gantry table and can follow the patient.

An example includes a table-mounted patient display. The display enables a patient to see video while the technologist is preparing the examination. Moreover, the video moves with the patient while the patient is being moved into the bore. Movement into a narrow and confined space can induce anxiety and claustrophobia, and distracting a patient with a video that moves with them may alleviate some of this anxiety.

Referring now to FIG. 1, an example system is illustrated for displaying images to a patient during a gantry-based medical imaging or therapeutic procedure. While the example embodiments of the present disclosure may be adapted to a wide range of gantry-based medical imaging and therapeutic systems, the example system shown in FIG. 1 includes a magnetic resonance scanner gantry 50 that employs a main magnet 52 to produce a main magnetic field B0, which generates a polarization in the patient 60. The example system includes gradient coils 54 for generating magnetic field gradients. A body coil 56 transmits radio frequency (RF) pulses to the patient 60 and receives RF signals coil from the patient. Alternatively, head coil or other coil (not shown) may be employed to radiate and/or detect RF pulses. The RF pulses are generated by an RF unit 65, and the magnetic field gradients are generated by a gradient unit 70.

The patient 60 resides on a table 10 that is positionable relative to the gantry 50. The table 10 may be manually positionable, or controllably positionable through one or more actuation mechanisms, such as motors, represented in FIG. 1 by a table actuator 40. The position of the table may be detected via one or more sensors, such as encoding sensors.

The example system of FIG. 1 includes an apparatus that is secured to the table 10. The example apparatus shown in the figure is a display apparatus 101 for displaying images to the patient 60 without causing position-dependent image scaling when the table 10 is translated. The example display apparatus 101 includes a projector 100 that is supported in a fixed position relative to the table 10, by a support frame 105, such that the projector 100 moves in unison with the table 10. The support frame 105 also supports a projection screen 110 onto which images are projected, such that the projection screen 110 is fixed relative to the projector 100 (and the table 10). The projection screen 110 may be formed, for example, from a translucent material that diffuses light, such as frosted glass or translucent plastic.

A viewing mirror 120 is placed such that the patient can view images projected onto the projection screen 110 through the viewing mirror 120. The viewing mirror 120 may be supported by the support projector housing (or via a support arm or link that is not shown in figure). In the illustrated example embodiment, the projector 100, the projection screen 110, and the viewing mirror 120 are supported in a mutually fixed relationship, and in a manner that is fixed relative to the table 10. As shown in FIG. 1, the fixed spatial relationship between the projector 100, the projection screen 110, and the viewing mirror 120 relative to the table 10 results in projected images that are viewable by the patient during translation of the table 10 such that the projected images maintain a fixed projected field size during translation. The fixed spatial relationship also maintains focus of the projected image during translation of the table 10, and avoids position-dependent overfilling of the projection screen 110.

In the example implementation shown in FIG. 1, the medical gantry is a magnetic resonance imaging gantry 50, and the projector 100 is magnetic resonance imaging compatible. Magnetic resonance compatibility can be achieved by avoiding the use of ferromagnetic materials and operating electronics in frequency ranges outside of the operating bandwidth of the magnetic resonance scanner. Electromagnetic shielding may also be employed to avoid or reduce electromagnetic interference. For example, large currents flowing through inductors may cause electromagnetic emissions. These emissions can be reduced by employing shielding around the inductors. In one example implementation, shielding be provided to achieve continuous shielding on a circuit board (i.e. shielding connected to the ground plane).

In some example implementations, magnetic resonance compatibility may be achieved by substituting conventional ferrite core inductors with alternative components, such as, but not limited to, ferrite-free inductors such as phenolic-core, polymer-core, ceramic-core, or carbonyl-core inductors.

In some example implementations, the projector may be battery powered or may be powered through an external power source. The projector may receive displayable content, such as movies, television, videos, and/or a user interface for selecting content to be displayed, via a wired connection, a wireless connector, or through media stored in internal memory.

It will be understood that the MRI system can have additional units or components that are not shown for clarity, such as, but not limited to, additional control or input devices, and additional sensing devices, such as devices for cardiac and/or respiratory gating. Furthermore, the various units can be realized other than in the depicted separation of the individual units. It is possible that the different components are assembled into units or that different units are combined with one another. Various units (depicted as functional units) can be designed as hardware, software or a combination of hardware and software.

In the example system shown in FIG. 1, control and processing hardware 200 controls the MRI scanner to generate RF pulses according to a suitable pulse sequence. The control and processing hardware 200 may include, for example, one or more processors 210, memory 215, a system bus 205, one or more input/output devices 220, and a plurality of optional additional devices such as communications interface 235, data acquisition interface 240, display 225, and external storage 230. The control and processing hardware 200 is interfaced with the MRI scanner gantry 50 for controlling the acquisition of the received MRI signals. The control and processing hardware 200 acquires the received MRI signals from the RF unit 65 and processes the MRI signals to perform image reconstruction and generate MRI images. The control and processing hardware 200 may be programmed with instructions in the form of a set of executable image processing modules, such as, but not limited to, a pulse sequence generation module 245, an image reconstruction module 250, a table position control module 260, and a media control module 270.

The pulse sequence generation module 245 may be implemented using algorithms known to those skilled in the art for pulse sequence generation. During MRI scanning, RF data is received from the RF coils 56. The pulse sequence generation module 245 establishes the sequence of RF pulses and magnetic field gradients depending on the desired imaging sequence, MR signals responsively emitted by the patient and detected by the coils 56 are acquired. The image reconstruction module 245 processes the acquired MRI signals to perform image reconstruction and MRI image generation.

In some example embodiments, the control and processing hardware, or addition control circuitry, may be employed to control the position of the table relative to the gantry. For example, the table position may be controlled by the table position control module 260 the control and processing hardware 200 by sending signals to the table actuator 40. The table position may by controlled in a closed-loop manner based on feedback obtained from one or more table position sensors. It will be understood that table orientation (e.g. one or more table angles) may additionally or alternatively be controlled.

In some example embodiments, the control and processing hardware, or addition control circuitry, may be employed to deliver displayable image content (media content) to the projector 100. For example, the media control module 270 may be employed to control the delivery of media content to the projector 100, through a wired or wireless connection. The media control module 270 may be employed to facilitate connection to a remote media delivery service, such as a remote media streaming service, through a connection to the internet.

Figure 2:
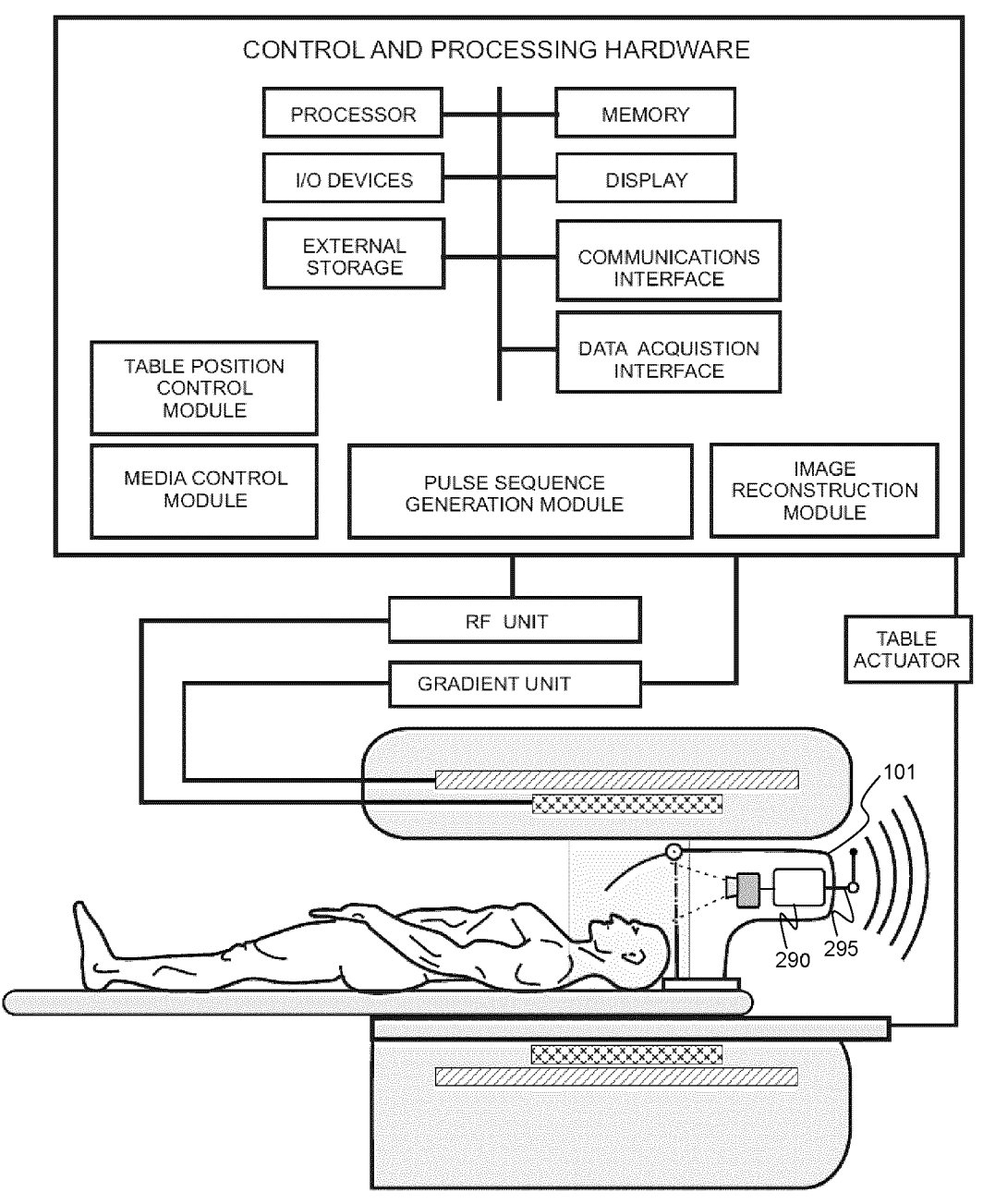

It is to be understood that the example system shown in FIG. 1 is illustrative of a non-limiting example embodiment, and is not intended to be limited to the components shown. For example, the system may include one or more additional processors and memory devices. Furthermore, one or more components of control and processing hardware 200 may be provided as an external component that is interfaced to a processing device. For example, FIG. 2 illustrates an alternative example embodiment in which the display apparatus 101 includes a wireless receiver or transceiver 290 and an antenna 295.

Figure 3A:
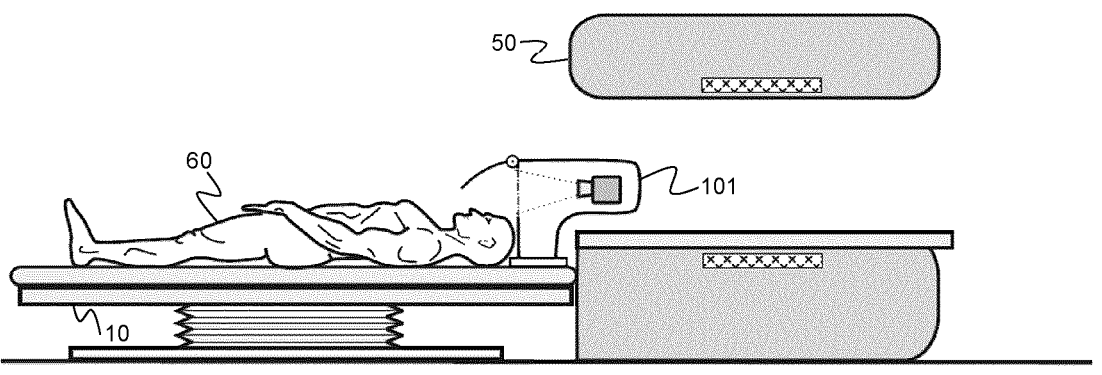
FIGS. 3A-3C illustrate the process of moving the table to position a subject within the gantry.
Figure 3B:
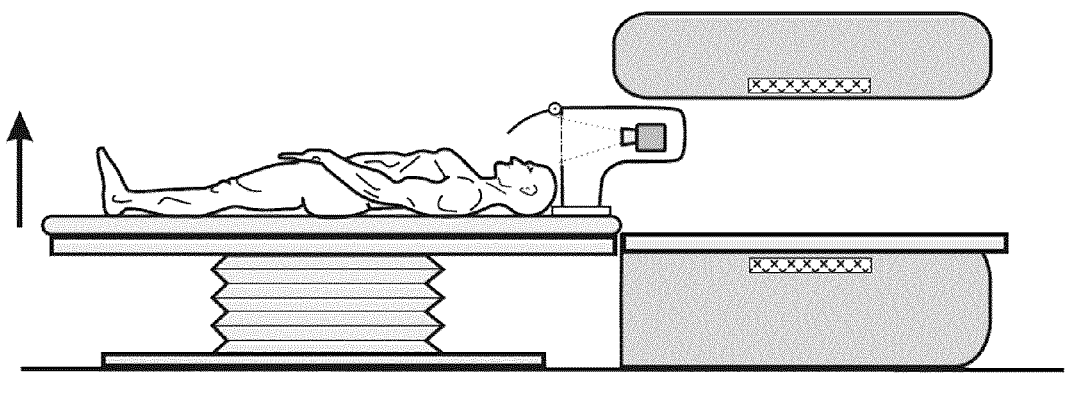
Figure 3C:
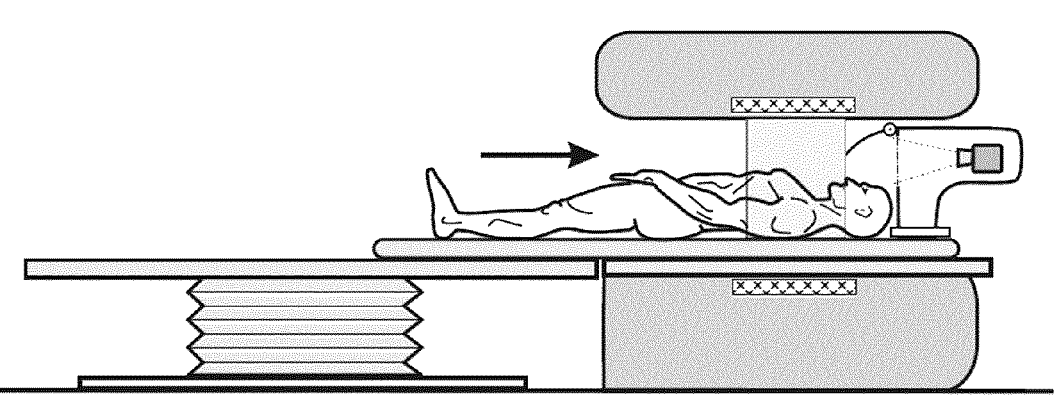

FIGS. 3A-3C illustrate the process of positioning a subject 60, residing on the table 10, within the gantry 50 of an MRI scanner. In the illustrated example, a head-first imaging application is shown, in which the subject's head is located close to the end of the table 10. As a result, limited space is available beyond the subject's head, and a distal portion of the apparatus extends beyond a longitudinal end of the table 10.

When the table 10 is in the home position, the end of the table lines up with the bore entrance. As a result, equipment is still located in the bore. As shown in FIG. 3A, the table 10 can be lowered to enable the patient to get on and off the table more easily. If this is procedure is performed properly, the table is lowered without causing a collision with the distal portion of the apparatus that overhangs the end of the table.

Figure 4A:
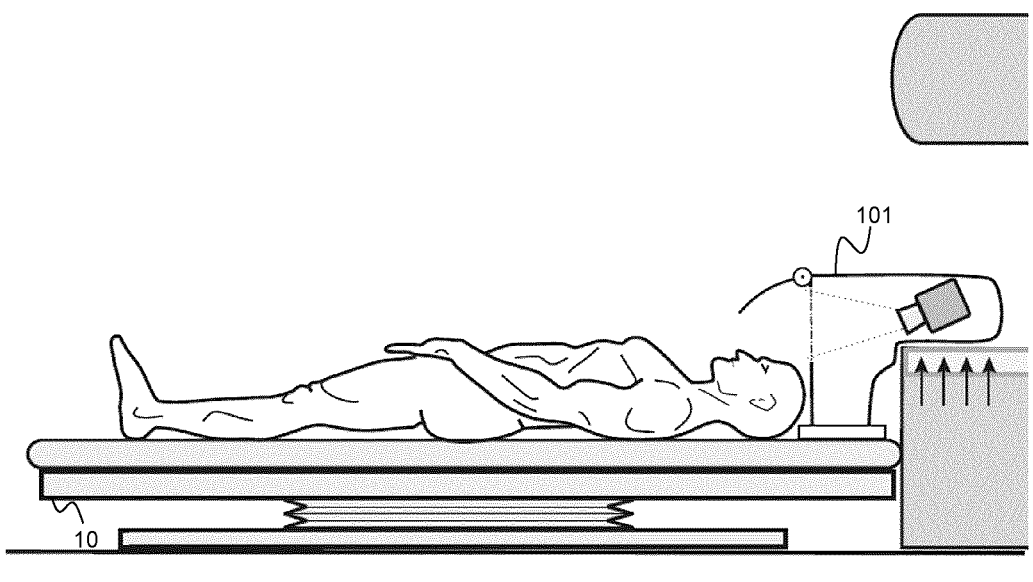
FIGS. 4A and 4B illustrate a vertical collision that occurs due to downward motion of the table, such that a distal portion of the apparatus that extends beyond the longitudinal end of the table contacts a lower inner surface of the gantry.
Figure 4B:
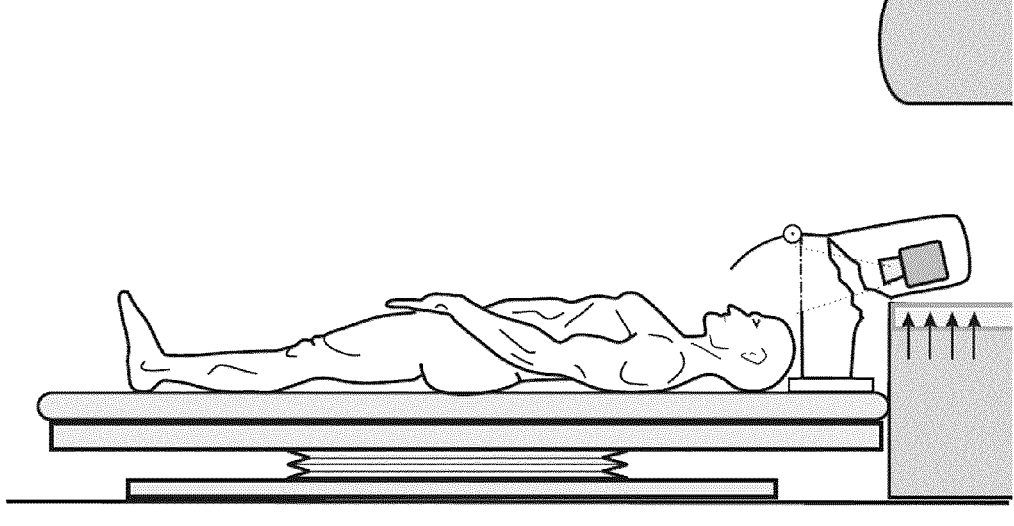

However, in the event that the table 10 is inadvertently lowered further, a collision occurs as the distal portion of the apparatus 101 contacts the inside bottom surface of the MRI bore, as shown in FIG. 4A. If the apparatus 101 is firmly secured to the table 10, the upwardly-directed force of the collision resulting from the downward motion of the table 10 can cause mechanical buckling of one or more components of the apparatus 101, thereby presenting significant risk to the subject, as shown in FIG. 4B. As some MRI systems can be installed on pedestals that raise the MRI system above the floor, such a configuration raises the MRI bore with respect to the lowest table position, further decreasing the distance the table can be lowered without a collision. Another collision risk arises when the table extends from the MRI bore or is withdrawn from the MRI bore, which presents the risk of a horizontal collision with objects such as walls, door frames, furniture and other equipment.

The present inventors set out to develop solutions that would avoid or mitigate risks associated with such collisions, in order to prevent or reduce the likelihood of injury to the subject and damage to equipment. Accordingly, various example embodiments of the present disclosure provide systems and methods that accommodate forces associated with collisions involving an apparatus supported by a table associated with a gantry of a medical imaging or therapeutic system.

In some example embodiments, a system is provided that includes a gantry supporting a medical imaging device or a medical therapeutic device and a table translatable relative to the gantry. The example system also includes an apparatus that is secured to the table such that a distal portion of the apparatus extends beyond a longitudinal end of the table. In order to accommodate a force applied to the distal portion of the apparatus during a collision with an object during motion of the table, a pivot joint is provided such that the force results in rotation of a portion of the apparatus about the pivot joint. The rotatable portion that rotates about the pivot joint includes at least the distal portion the apparatus. Various example embodiments of the present example solution are described in detail below.

Figures 5A, 5B, 5C, 5D, 5E, 5F:
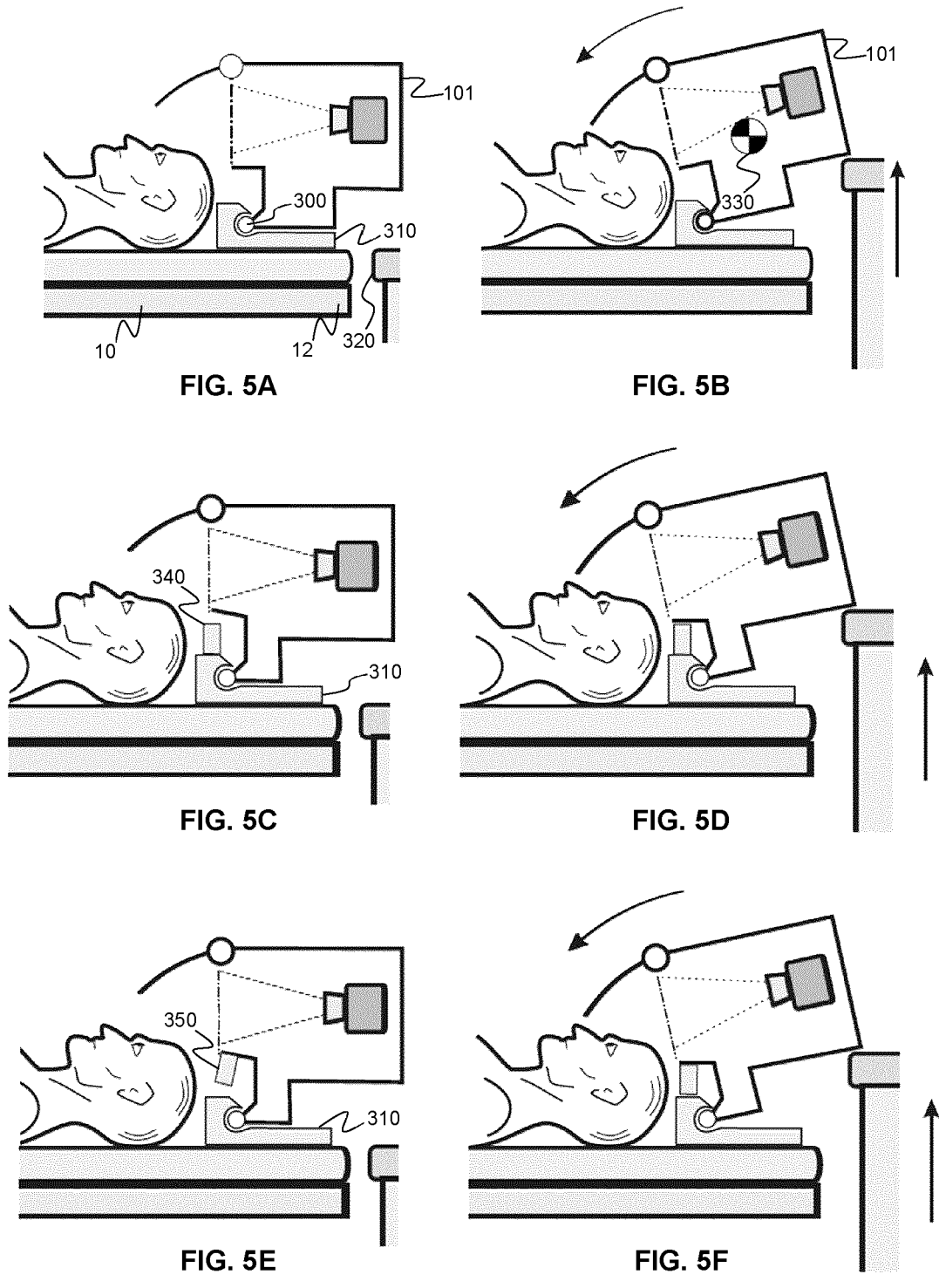
FIGS. 5A-5L illustrate several example embodiments in which at least a portion of the apparatus is capable of rotating under application of an external force during a collision.

Referring first to FIG. 5A, an example embodiment is shown in which a display apparatus 101 is secured to the table via a connection member 310. The connection member 310 may be secured to a guide rail of the table (not shown). In the example embodiment shown in FIG. 5A, a pivot joint 300 is provided such that the apparatus 101 is pivotable relative to the connection member 310, and thus relative to the table 10, in the presence of force applied to the distal region of the apparatus 101 (the portion of the apparatus that overhangs the longitudinal end 12 of the table).

For example, in the case of a vertical collision involving an upwardly-directed force applied by the lower inner surface 320 of the gantry when the table is excessively lowered, a torque is applied to the apparatus 101 about the pivot joint, which in turn causes rotation of the apparatus, as shown in FIG. 5B. Notably, the ability to passively accommodate rotation in the presence of the applied force during the collision (i.e. without active collision sensing and/or automated collision avoidance mechanisms) avoids the buildup or concentration of forces and the unpredictable and dangerous mechanical buckling of one or more components of the apparatus, which can otherwise cause harm to the subject and damage to equipment. As explained further below, the example embodiments illustrated in FIGS. 5A-5L may be employed to passively and rotationally accommodate a horizontal force resulting from a horizontal collision (e.g. with a wall) during horizontal motion of the table.

Although FIGS. 5A and 5B show a single pivot joint, it will be understood that an additional pivot joint may be provided on an opposing side of the table (in a direction into the page of the figure). For example, the apparatus may be secured to the table through a pair of connection members that are respectively received within two channels of the table, such that the apparatus may be pivotally coupled to each connection member through a respective pivot joint.

As shown in FIG. 5B, the center of gravity 330 of the rotatable portion of the apparatus 101 may be located such that when the rotatable portion of the apparatus reaches a maximum angle due to the collision, a gravitational torque is applied to the rotatable portion that opposes further rotation of the rotatable portion.

Figures 5G, 5H, 5I, 5J, 5K, 5L:
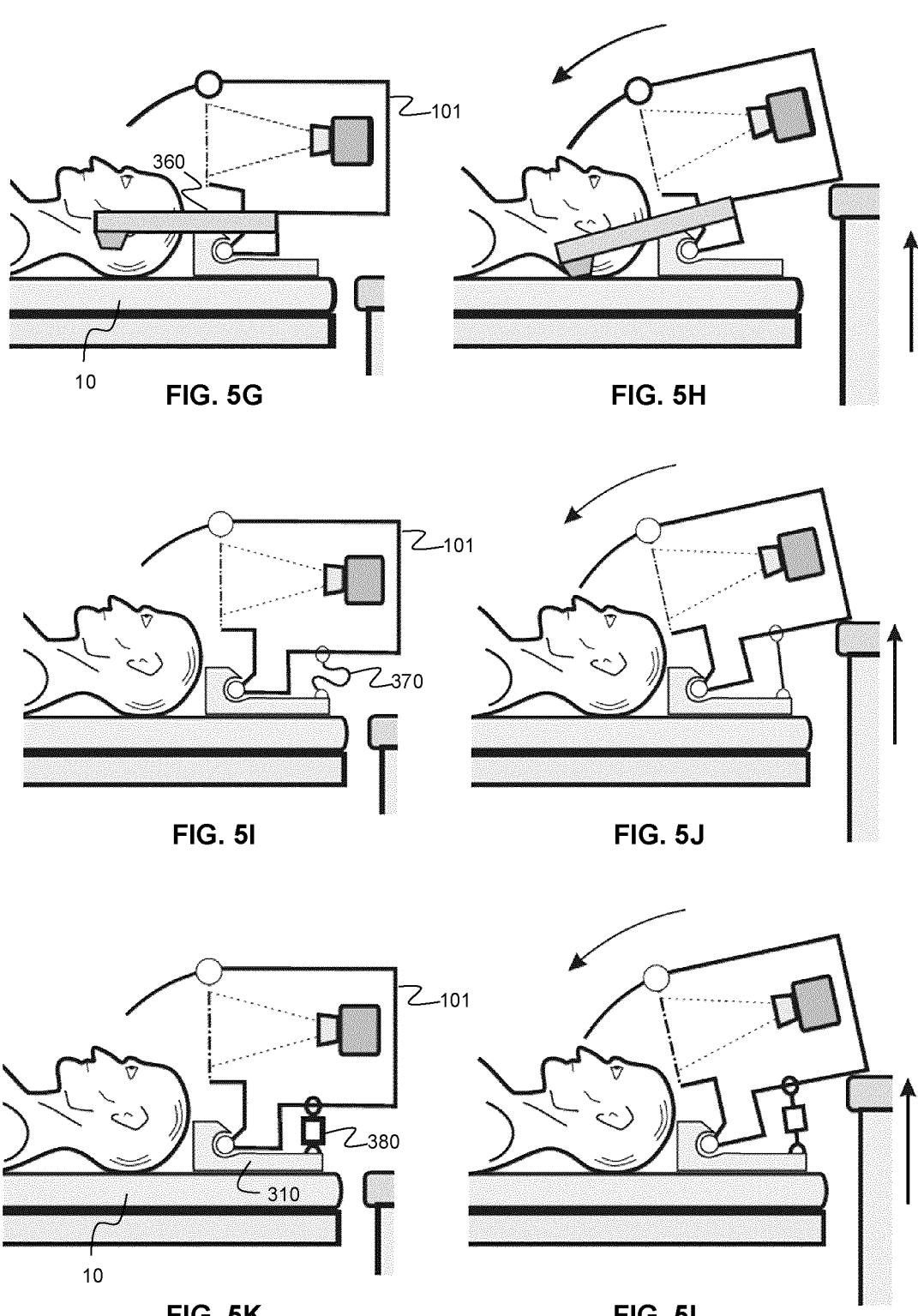

FIGS. 5C-5J illustrate several non-limiting and example embodiments in which a stop means is provided for arresting rotation of the rotatable portion of the apparatus beyond a pre-selected rotation angle. In FIGS. 5C and 5D, a structural stop 340 is provided on the connection member 310 to limit rotation of the apparatus about the pivot joint. In FIGS. 5E and 5F, a stop member 350 extends from the apparatus to contact the connection member 310 when the apparatus is rotated beyond a pre-selected pivot angle. In FIGS. 5G and 5H, another stop member 360 extends from the apparatus to contact the table 10 (or a mattress residing on the table) when the apparatus is rotated beyond a pre-selected pivot angle. In FIGS. 5I and 5J, a cable 370 extends from the apparatus to the connection member 310 and becomes taught when the apparatus is rotated beyond a pre-selected pivot angle.

FIGS. 5K and 5L illustrate an example embodiment in which a restoring means is provided for applying a restoring torque to the rotatable portion of the apparatus. A viscous (e.g. dashpot) or elastic (e.g. spring) element 380 is provided between the apparatus 101 and the connection member 310 (or, for example, between the apparatus and the table 10), thereby providing restoring torque that opposes rotation of the apparatus about the pivot element. Another example of a restoring mechanism is a torsion spring that can be provided in association with the pivot joint.

In other example embodiments, a resistance element can be included that resists rotation of the rotatable portion of the apparatus beyond a pre-selected rotation angle. For example, the resistance element can be a compressible stop or, for example, an elastic cable connecting the rotatable portion to a non-rotatable portion of the system such that the elastic cable becomes taught when the rotatable portion is rotated to the pre-selected rotation angle.

Although many of the example embodiments described herein relate to a display apparatus, it will be understood that the example embodiments may be adapted to a wide variety of different apparatus and devices that are configured to be secured to a table of a medical imaging and/or therapeutic system.

Referring now to FIGS. 6A-6D, several additional example embodiments are illustrated in which at least a portion of the apparatus 101 is capable of rotating under application of an external force during a collision, where the pivot joint is provided at an intermediate location of the apparatus. In FIGS. 6A and 6B, the pivot joint 385 is located along an upper surface of the apparatus 101. In this example embodiment, the pivot joint 385 is located such that the rotatable portion 101A comprises one or more electrical components and wherein a remaining non-rotatable portion 101B of the apparatus is absent of active electrical components. In FIGS. 6C and 6D, the pivot joint 390 is located above support member portion 395 of the apparatus.

Figures 7E, 7F, 7G, 7H, 7I, 7J:
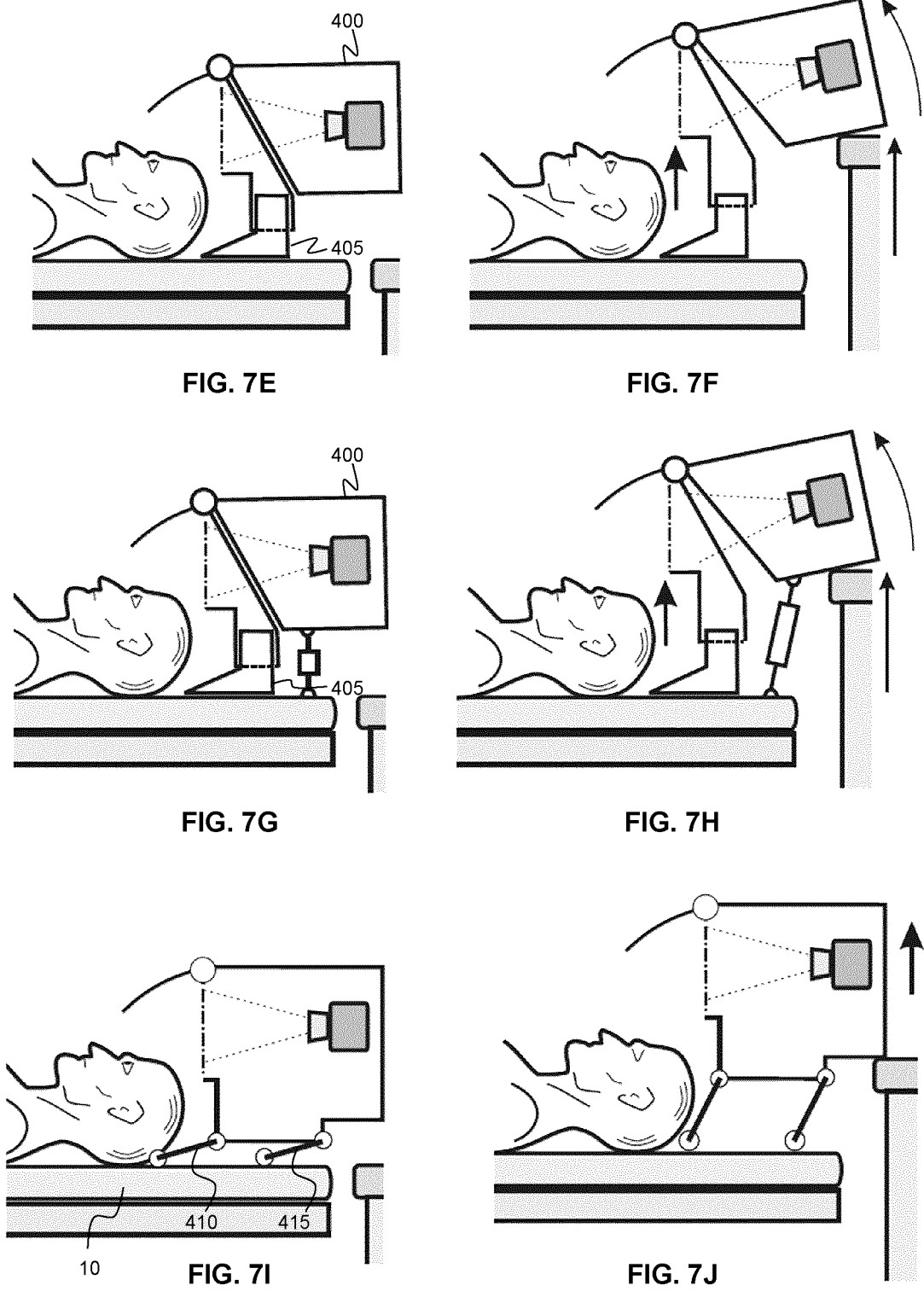
FIGS. 7E-7J illustrate several example embodiments in which at least a portion of the apparatus is capable of translating and rotating under application of an external force during a collision.

Referring now to FIGS. 7A-7D, various example embodiments are illustrated in which a portion of the apparatus that includes the distal region is translatable under application of a force resulting from a collision. FIGS. 7A and 7B illustrate an example embodiment in which the translatable portion 400 of the apparatus is telescopically extendable from another portion 405 of the apparatus that is fixed to the table. FIGS. 7C and 7D illustrate an example embodiment that incorporates a viscous or elastic resistance mechanism 380, such as those described with reference to FIGS. 6C and 6D.

7E to 7H show additional example embodiments, combining concepts from FIGS. 7A-7D and 6A-6B, such that the apparatus is rotatable and translatable when a force is applied during a collision. FIGS. 7I and 7J illustrate another example embodiment in which the apparatus 101 is pivotally coupled to the table 10 by at least two adjacent pivot bars 410 and 415, each pivot bar being pivotally coupled to the apparatus and pivotally coupled to the table, such that under application of the force, the two adjacent pivot bars rotate in parallel and the rotatable portion of the apparatus is responsively rotated and translated.

Figures 8A, 8B, 8C, 8D, 8E, 8F, 8G, 8H, 8I, 8J, 8K, 8L:
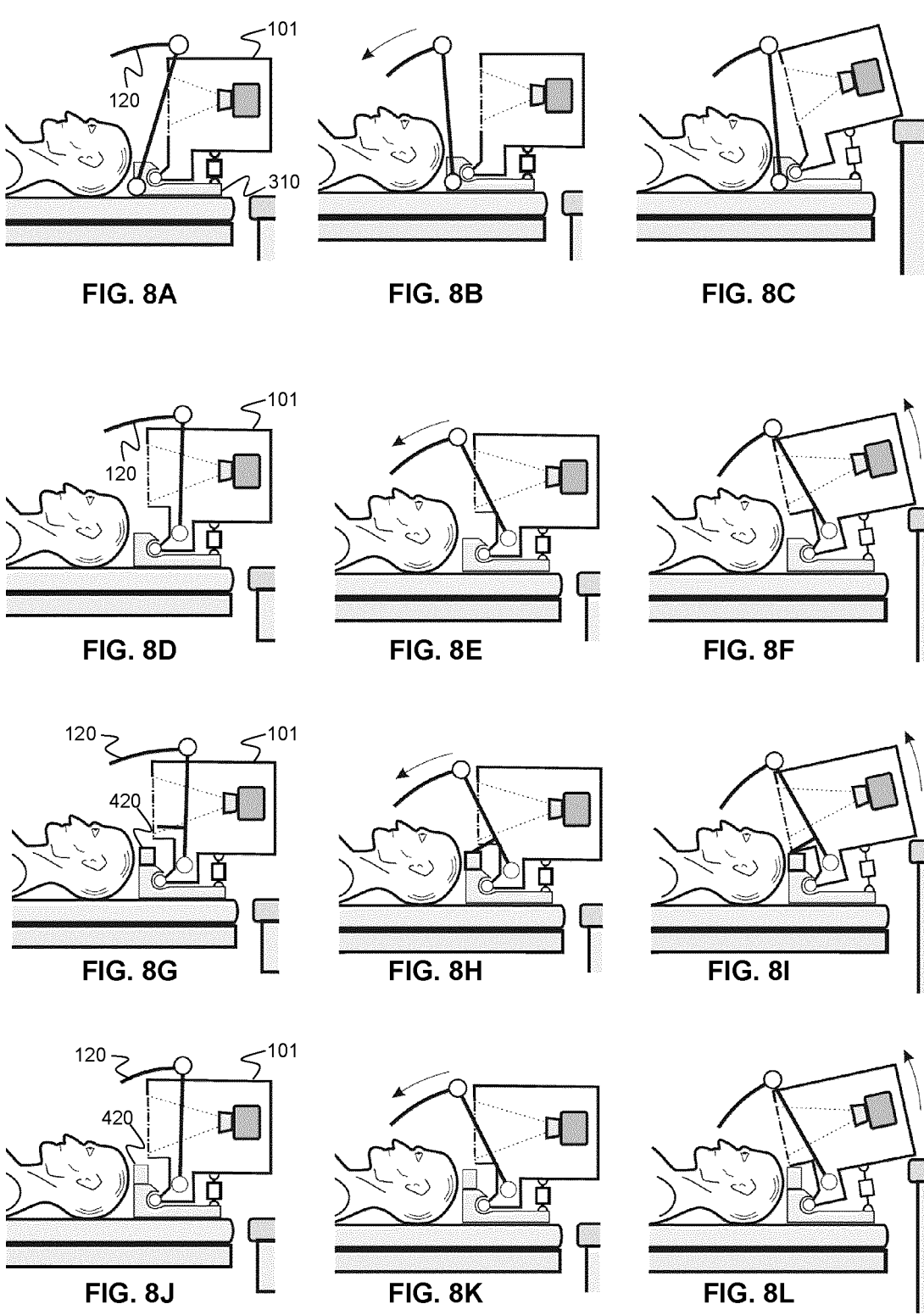
FIGS. 8A-8L illustrate several example embodiments in which at least a portion of the apparatus having a viewing mirror is capable rotating under application of an external force during a collision.

FIGS. 8A-8L illustrate several example embodiments in which the apparatus is a display apparatus that includes a viewing mirror, and where the display apparatus is capable rotating under application of an external force during a collision. In FIGS. 8A-8C, the viewing mirror 120 is independently supported by the connection member 310, such that a force applied to the distal region of the apparatus does not impact the viewing mirror. In FIGS. 8D-8F, the viewing mirror 120 is supported by the main body of the apparatus 101, such that a force applied to the distal region of the apparatus causes the viewing mirror to rotate in unison with the rotatable portion of the apparatus. FIGS. 8G-8I, illustrate an example embodiment in which the viewing mirror 120 is supported by the main body of the apparatus 101, and where the rotation of both the viewing mirror and the main body of the apparatus 101 is arrested beyond a prescribed angle by a common structural stop 420. FIGS. 8G-8I, illustrate an example embodiment in which the viewing mirror 120 is supported by the main body of the apparatus 101, and where the rotation of only the main body of the apparatus 101 is arrested beyond a prescribed angle by the structural stop.

Figures 9A, 9B:
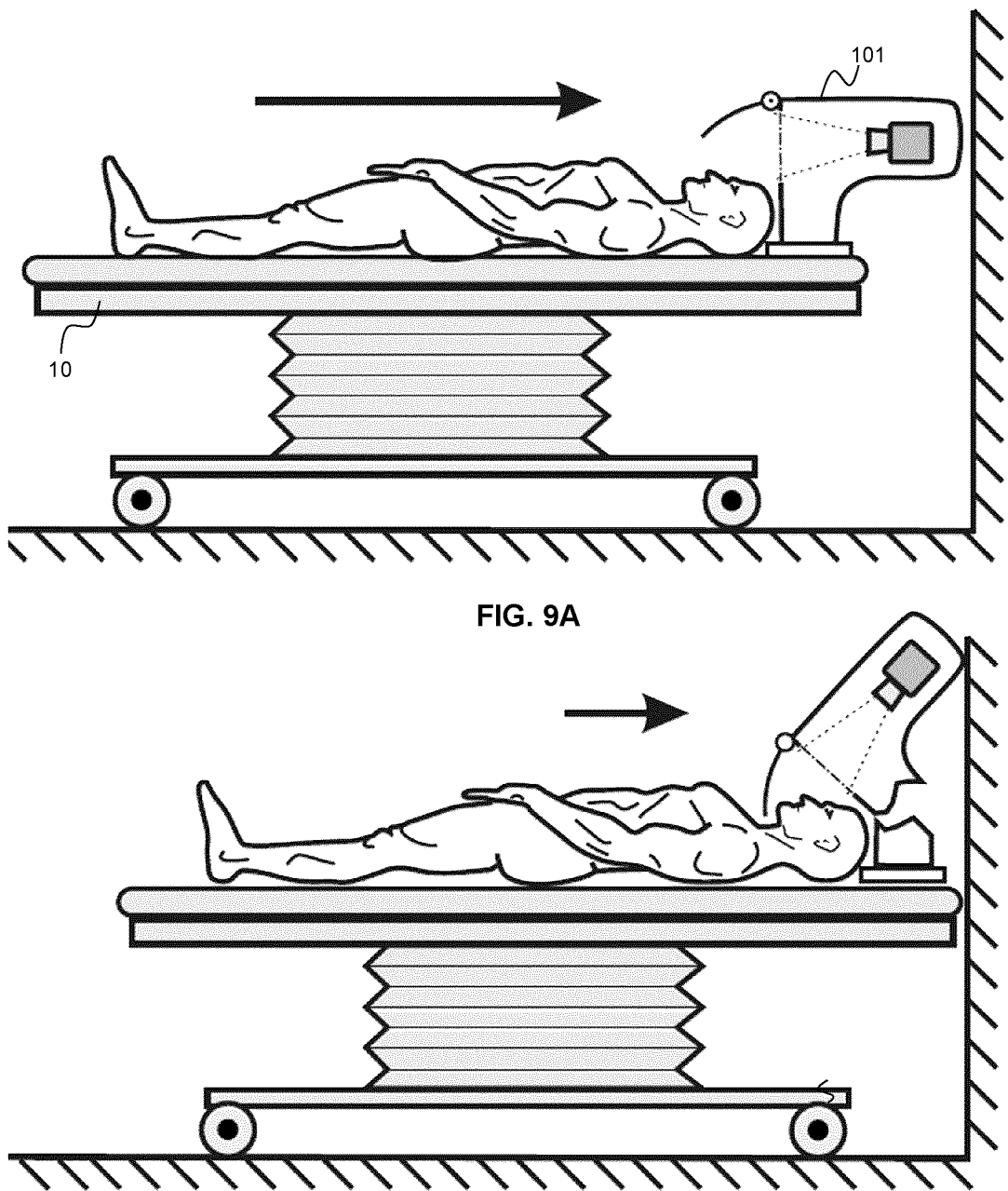
FIGS. 9A and 9B illustrate a horizontal collision that occurs due to horizontal motion of the table, such that a distal portion of the apparatus that extends beyond the longitudinal end of the table contacts a wall.

FIGS. 9A and 9B illustrate a horizontal collision that occurs due to horizontal motion of the table 10, such that a distal portion of the apparatus that extends beyond the longitudinal end of the table contacts a wall, illustrating the breakage of the apparatus due to the collision force.

Figures 10A, 10B:
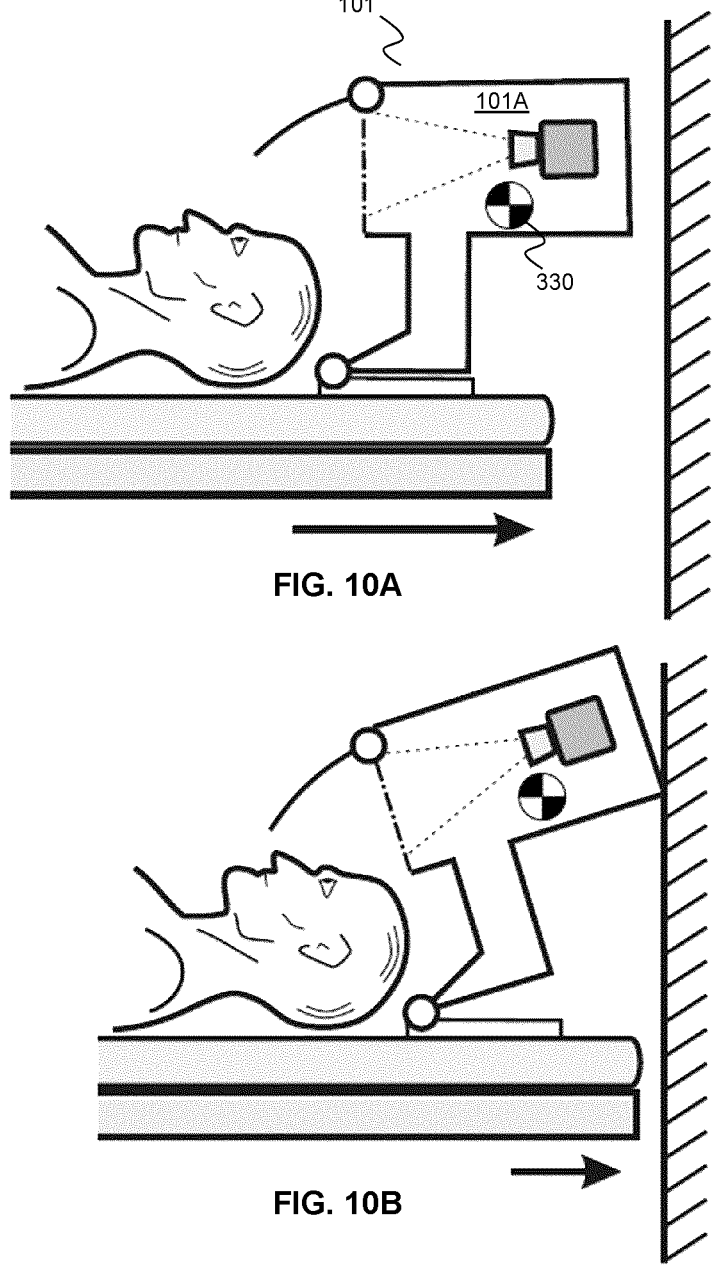
FIGS. 10A-10J illustrate several example embodiments in which at least a portion of the apparatus is capable rotating under application of an external force during a horizontal collision with a wall.
Figures 10C, 10D:
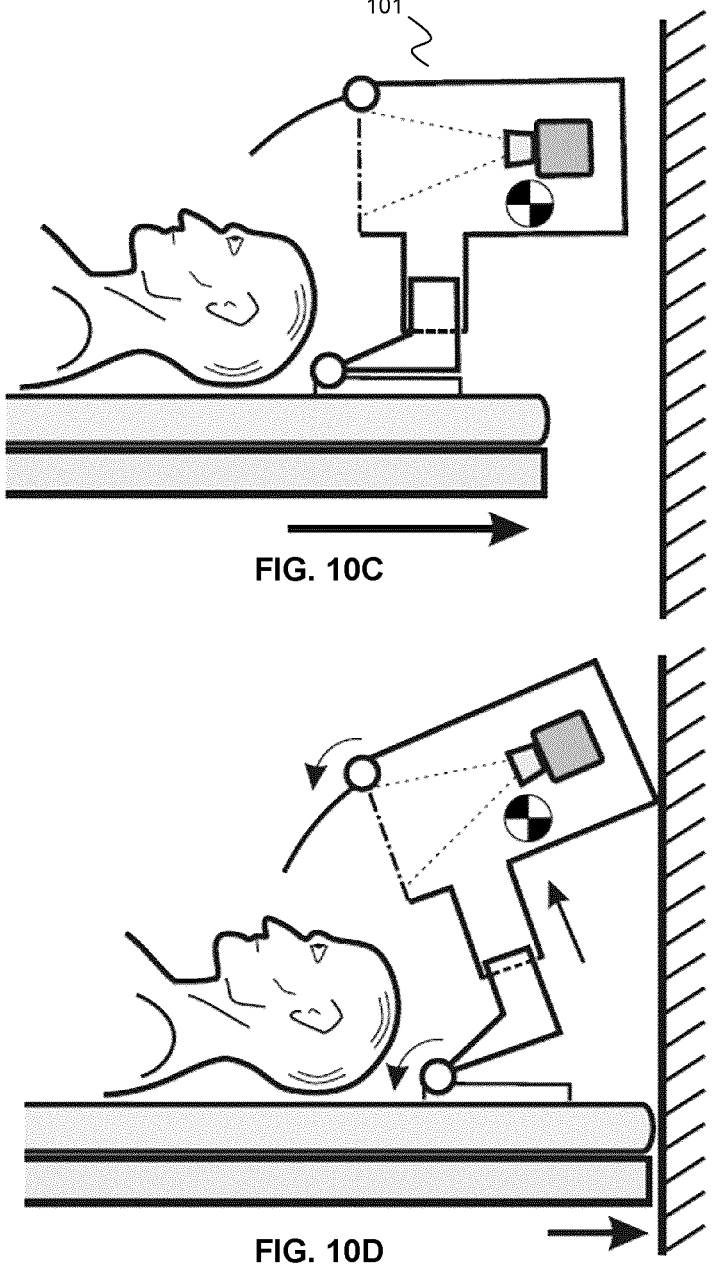
Figures 10E, 10F:
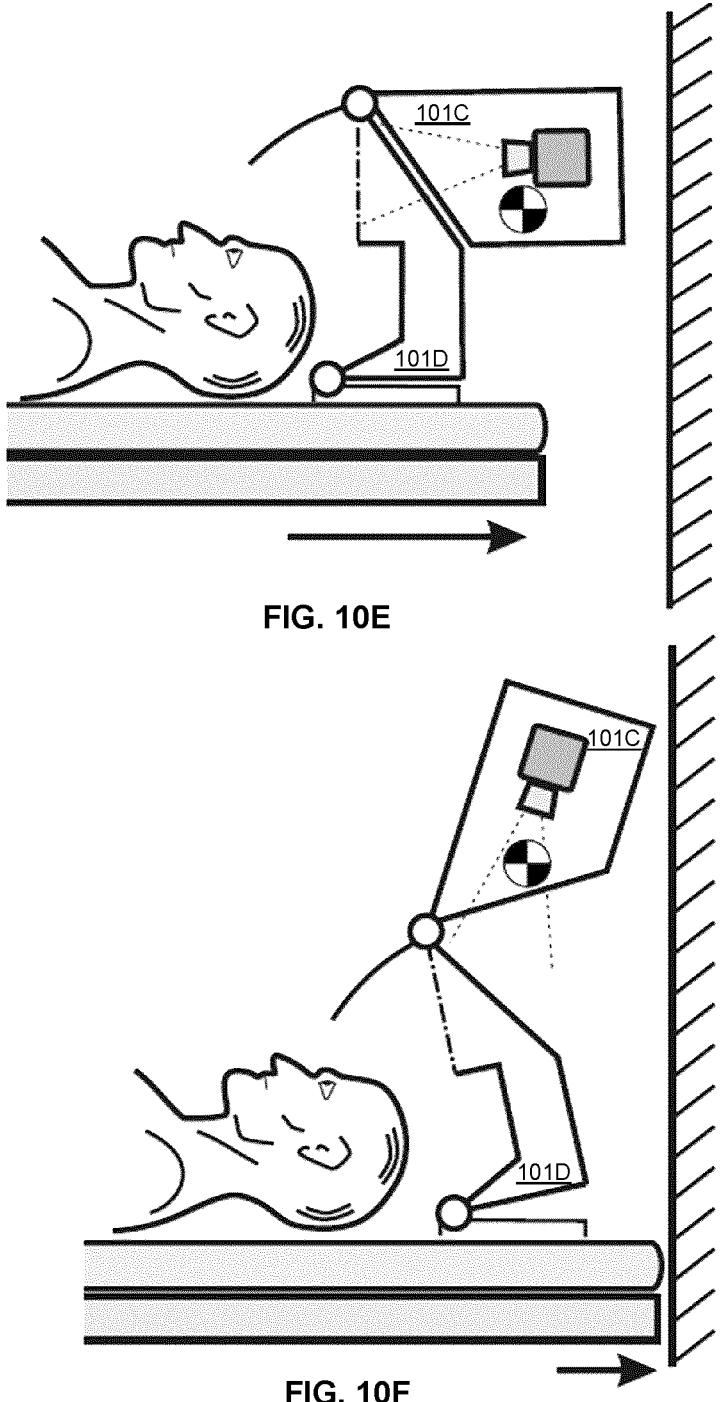
Figures 10G, 10H:
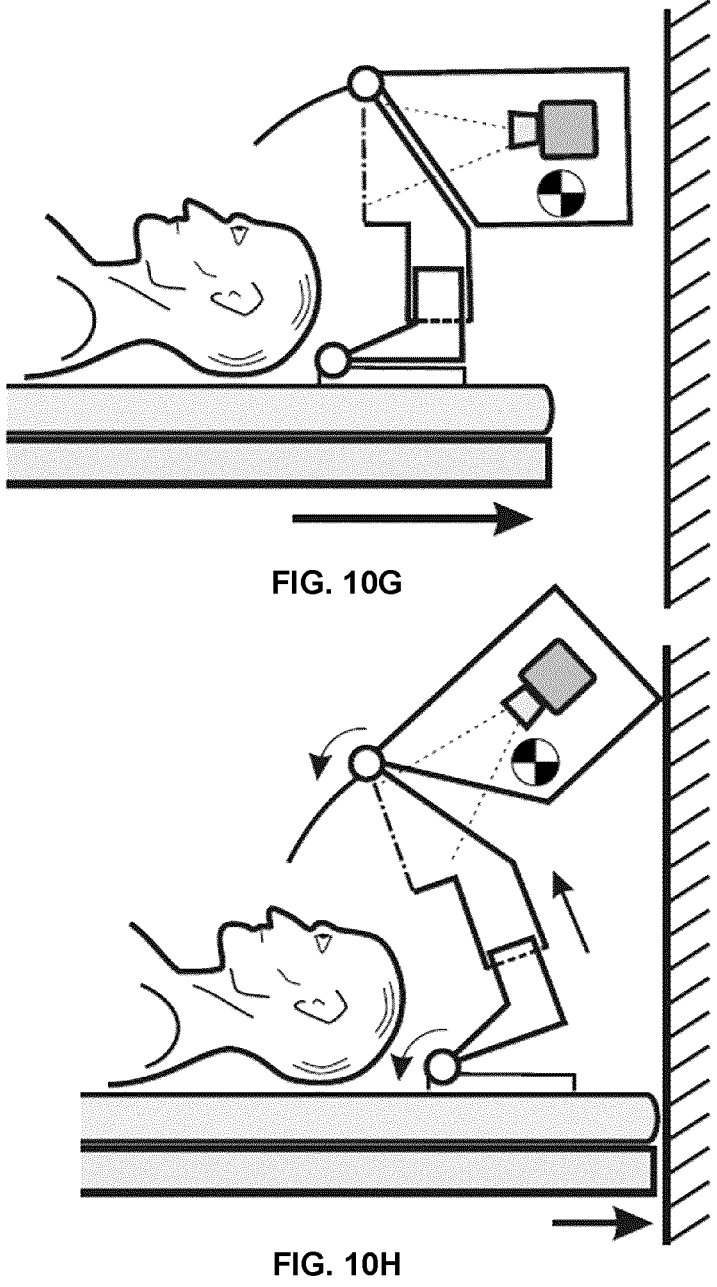
Figures 10I, 10J:
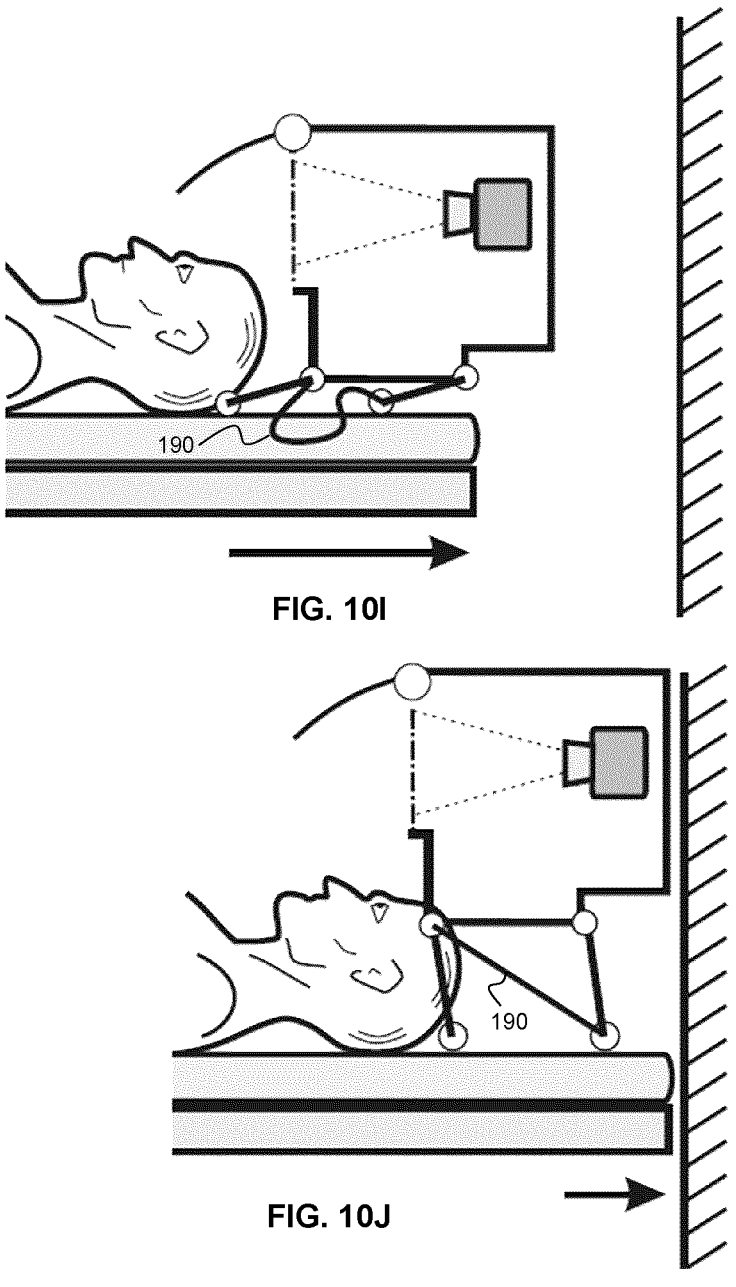
Figure 12A:
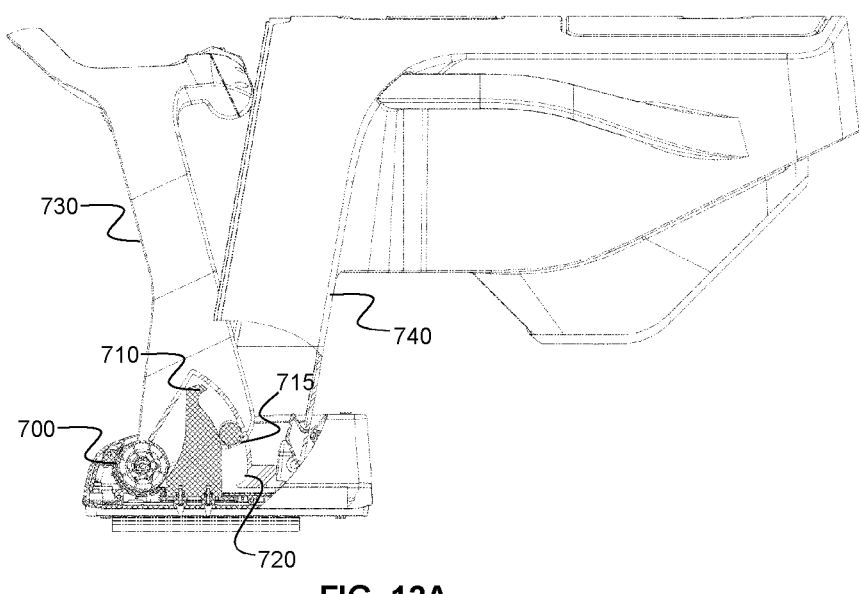
FIGS. 12A-12D illustrate example embodiment of a projection apparatus that is capable of rotating under application of an external force during a collision.
Figure 12B:
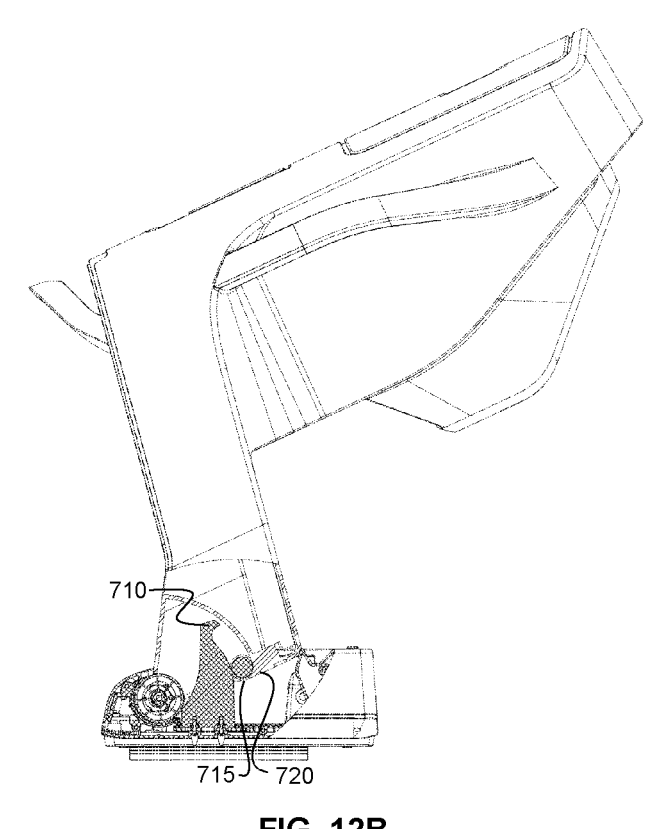
Figure 12C:
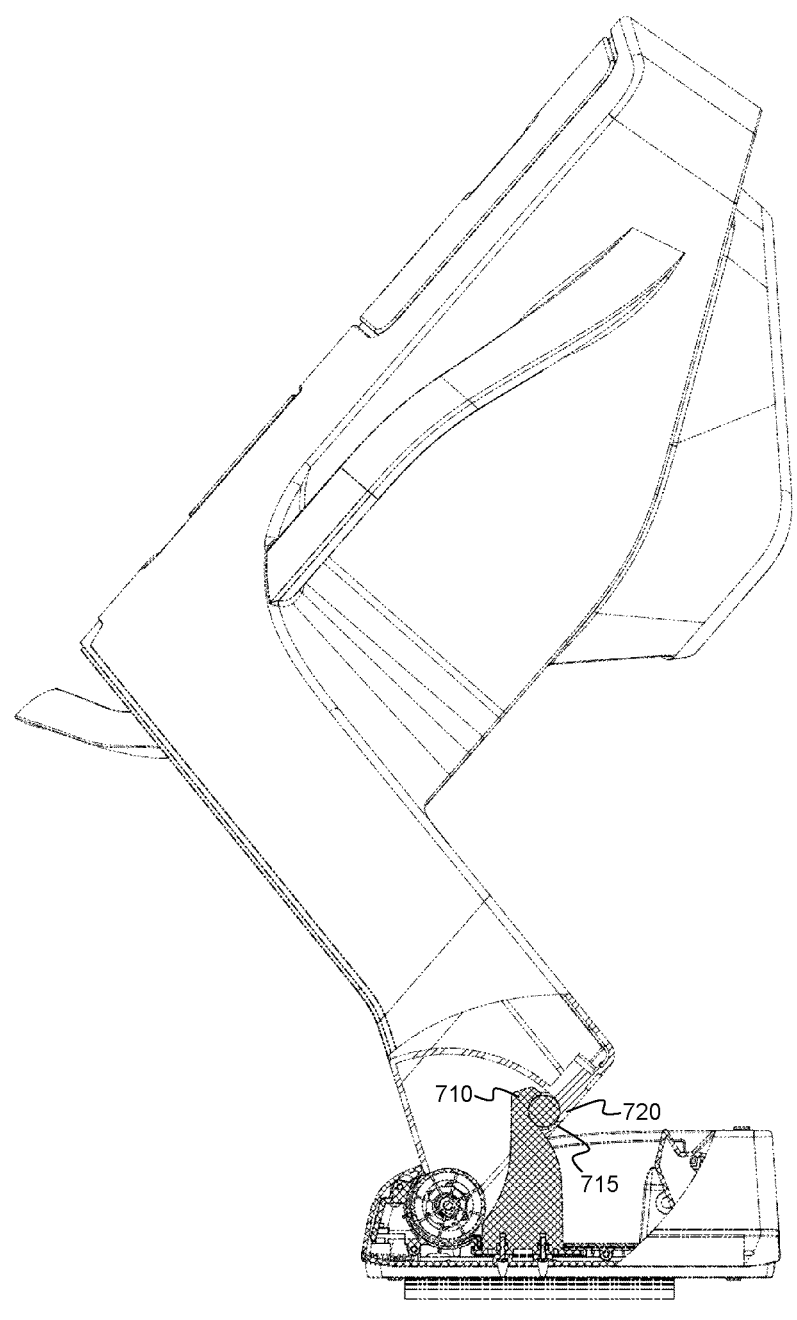
Figure 12D:
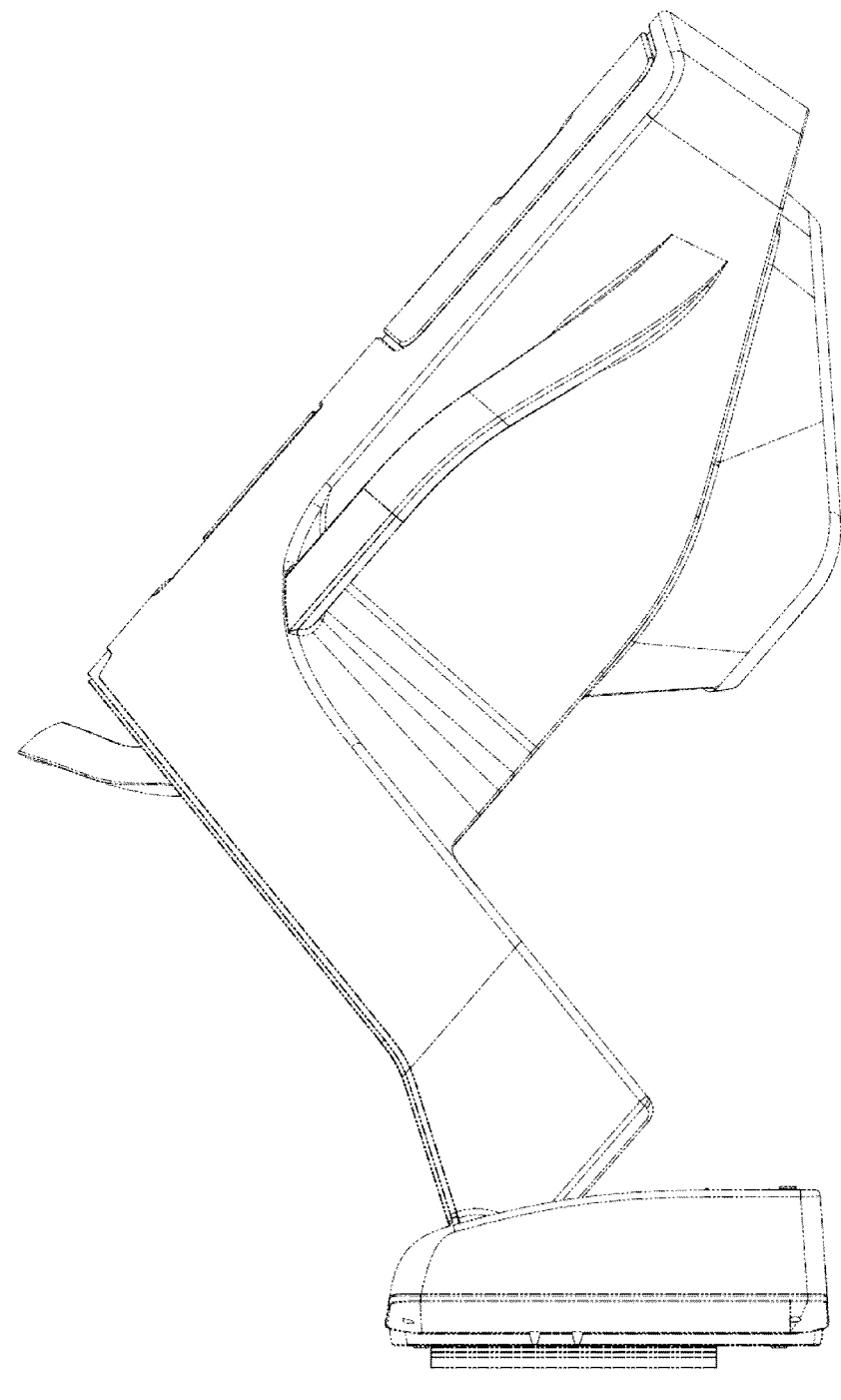

FIGS. 10A-10J illustrate several example embodiments in which at least a portion of the apparatus 101 is capable rotating under application of an external force during a horizontal collision with a wall. FIGS. 10A and 10B illustrate an example embodiment similar to that of FIGS. 5A and 5B. As can be seen in FIG. 10B, the center of gravity 330 of the rotatable portion 101A of the apparatus is located such that when the longitudinal end of the table contacts the wall during the horizontal collision and further horizontal translation of the apparatus is prevented, a gravitational torque applied to the rotatable portion 101A opposes further rotation of the rotatable portion. FIGS. 10C and 10D illustrate an example embodiment similar to that of FIGS. 7E-7H, in which rotation and translation of the apparatus occur under application of the collision force from the wall. FIGS. 10E and 10F illustrate an example embodiment in which the apparatus is formed from two independently rotatable portions 101C and 101D that are each capable of rotating in response to a collision, while FIGS. 10G and 10H show an example embodiment that also permits translation. FIGS. 10I and 10J illustrate an example embodiment similar to that shown in FIGS. 7I-7J, with the addition of a retention cable 190 that limits an amount of rotation and translation of the apparatus.

FIG. 11A illustrates a vertical collision that occurs due to upward motion of the table, such that a distal portion of the apparatus that extends beyond the longitudinal end of the table contacts an upper inner surface of the gantry. FIGS. 11B and 11C show an example embodiment in which the apparatus is configured to detach from the pivot joint when a downwardly-directed force exceeds a threshold force. For example, as shown in FIGS. 11B and 11C, the apparatus may be coupled to the pivot joint by a frangible portion 600 that is configured to break upon application of a sufficiently high force.

FIGS. 12A-12D illustrate example embodiment of a projection apparatus that is capable of rotating about a pivot joint 700 under application of an external force during a collision. The apparatus includes a main display portion 740 and a viewing mirror support 730, where rotation of both the main display portion 740 and the viewing mirror support 730 are constrained beyond a prescribed maximum rotation angle via a common stop member 710 that contacts feature 715 of the viewing mirror support 730, which in turn contacts feature 720 of the main display portion 740, as shown in the sequence of rotation illustrated in FIGS. 12A-12C.

It will be understood that the example passive collision accommodation mechanisms disclosed above are not intended to be limited to patient displays. Other non-limiting examples of equipment include patient monitoring systems, MR-guided surgical systems, MR-guide high frequency ultrasound systems, remote robotic device navigation systems, MR-compatible incubation systems, MR-compatible anesthetic delivery systems, other types of patient displays.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefor what is claimed is:

1. A display system comprising:
a display subsystem;
an attachment mechanism for securing said display subsystem to a table such that images displayed by said display subsystem are viewable by a subject when the subject resides in a supine position on the table;
said attachment mechanism being capable of attaching said display subsystem to the table such that a distal portion of said display subsystem extends beyond a longitudinal end of the table; and
wherein at least one of said attachment mechanism and said display subsystem comprise a pivot joint configured such that when said display subsystem is attached to the table such that the distal portion extends beyond a longitudinal end of the table, a force applied during a collision involving contact of said distal portion with an object results in rotation of a rotatable portion of said display subsystem about said pivot joint, thereby passively accommodating the applied force and preventing or reducing mechanical buckling of said display subsystem in the presence of the applied force; and
wherein said display subsystem comprises a projector and a screen, said attachment mechanism being capable of attaching said display subsystem to the table such that at least a portion of said projector resides within the distal portion extending beyond a longitudinal end of the table.

2. The display system according to claim 1 configured such that when the display subsystem is attached to the table with the distal portion of said display subsystem extending beyond the longitudinal end of the table and the collision is a vertical collision resulting from downward motion of the table and the force comprises an upwardly-directed force, said rotatable portion rotates about said pivot joint in response to application of the upwardly-directed force.

3. The display system according to claim 1 configured such that when the display subsystem is attached to the table with the distal portion of said display subsystem extending beyond the longitudinal end of the table, the collision is a horizontal collision resulting from horizontal motion of the table and the force is a horizontally-directed force, said rotatable portion rotates about said pivot joint in response to application of the horizontally-directed force.

4. The display system according to claim 1 wherein said attachment mechanism is configured to be secured to the table through a connection member, and wherein said display subsystem is pivotally coupled to said connection member through said pivot joint.

5. The display system according to claim 1 wherein said attachment mechanism is configured such that said display subsystem is secured to said table through a pair of connection members.

6. The display system according to claim 1 wherein said pivot joint is located at an intermediate location within said display subsystem.

7. The display system according to claim 6 wherein said intermediate location resides along an upper surface of said display subsystem.

8. The display system according to claim 6 wherein said pivot joint is located such that said rotatable portion comprises one or more electrical components and wherein a remaining non-rotatable portion of said display subsystem is absent of active electrical components.

9. The display system according to claim 6 wherein said rotatable portion is a first rotatable portion and said pivot joint is a first pivot joint, said display subsystem further comprising a second rotatable portion that is pivotally connected to said first rotatable portion through said first pivot joint, and wherein said second rotatable portion is pivotally connected to said table through a second pivot joint, such that both said first rotatable portion and said second rotatable portion are rotatable in response to application of the force.

10. The display system according to claim 1 further comprising a restoring means for applying a restoring torque to said rotatable portion of said display subsystem.

11. The display system according to claim 10 wherein said restoring means comprises an elastic member connecting said rotatable portion to a non-rotatable portion of said display subsystem.

12. The display system according to claim 10 wherein said restoring means comprises a damping member connecting said rotatable portion to a non-rotatable portion of said display subsystem.

13. The display system according to claim 10 wherein said restoring means comprises a torsion spring.

14. The display system according to claim 1 wherein said display subsystem is configured to be pivotally coupled to the table by at least two adjacent pivot bars, each pivot bar being pivotally coupled to said apparatus and pivotally coupled to said table, such that under application of the force, said at least two adjacent pivot bars rotate in parallel and said rotatable portion of said apparatus is rotated and translated.

15. The display system according to claim 1 further comprising a stop means for arresting rotation of said rotatable portion beyond a pre-selected rotation angle.

16. The display system according to claim 15 further wherein said stop means comprises a structural member configured to arrest rotation of said rotatable portion beyond the pre-selected rotation angle.

17. The display system according to claim 16 wherein said structural member is attached to said rotatable portion of said display subsystem such that rotation of said rotatable portion is arrested upon contact of said structural member with the table.

18. The display system according to claim 16 wherein said structural member is attached to table such that rotation of said rotatable portion is arrested upon contact of said structural member with said rotatable portion of said display subsystem.

19. The display system according to claim 15 wherein said stop means comprises a cable connecting said rotatable portion to a non-rotatable portion of said system such that said cable becomes taught when said rotatable portion is rotated to the pre-selected rotation angle.

20. The display system according to claim 16 wherein the pre-selected rotation angle is selected to avoid contact of said display subsystem with a subject when the subject is positioned on the table such that a distal portion of the subject resides adjacent to said display subsystem.

21. The display system according to claim 1 further comprising a resistance means for resisting rotation of said rotatable portion beyond a pre-selected rotation angle.

22. The display system according to claim 21 wherein said resistance means comprises a compressible stop.

23. The display system according to claim 21 wherein said resistance means comprises an elastic cable connecting said rotatable portion to a non-rotatable portion of said system such that said elastic cable becomes taught when said rotatable portion is rotated to the pre-selected rotation angle.

24. The display system according to claim 1 wherein said display subsystem is configured such when the force is applied to said distal portion during the collision involving contact of said distal portion with the object during motion of the table, the force results in translation of at least said rotatable portion in addition to rotation of said rotatable portion of said display subsystem about said pivot joint.

25. The display system according to claim 24 wherein said display subsystem comprises a first portion that is secured to said table and a second portion that is telescopically extendable from the first portion when the force is applied to said distal portion.

26. The display system according to claim 1 wherein said display subsystem is configured such that when the collision is a vertical collision resulting from upward motion of said table and the force is a downwardly-directed force, said display subsystem is configured to detach from said pivot joint when the downwardly-directed force exceeds a threshold force.

27. A medical imaging and/or therapeutic system comprising:
    a gantry;
    a table translatable relative to said gantry; and
    the display system according to claim 1.

* * * * *